(12) United States Patent
Polvino et al.

(10) Patent No.: US 8,039,456 B2
(45) Date of Patent: *Oct. 18, 2011

(54) METHOD OF STIMULATING THE MOTILITY OF THE GASTROINTESTINAL SYSTEM USING IPAMORELIN

(75) Inventors: William J. Polvino, Tinton Falls, NJ (US); Richard Nelson, Morristown, NJ (US); William R. Mann, Sparta, NJ (US)

(73) Assignee: Helsinn Therapeutics (U.S.), Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/313,956

(22) Filed: Nov. 26, 2008

(65) Prior Publication Data

US 2009/0143310 A1 Jun. 4, 2009

Related U.S. Application Data

(63) Continuation-in-part of application No. 11/203,639, filed on Aug. 12, 2005, now abandoned.

(60) Provisional application No. 60/600,959, filed on Aug. 12, 2004, provisional application No. 61/008,828, filed on Dec. 21, 2007.

(51) Int. Cl.
   *A61K 31/33* (2006.01)
(52) U.S. Cl. ............................................. 514/183
(58) Field of Classification Search .................. 514/183
   See application file for complete search history.

(56) References Cited

U.S. PATENT DOCUMENTS

| | | | |
|---|---|---|---|
| 6,451,806 B2* | 9/2002 | Farrar | 514/282 |
| 2002/0042419 A1* | 4/2002 | Hakkinen | 514/249 |
| 2005/0277677 A1 | 12/2005 | Heiman et al. | |
| 2007/0021331 A1 | 1/2007 | Fraser et al. | |
| 2007/0191283 A1 | 8/2007 | Polvino | |
| 2007/0191289 A1 | 8/2007 | Fushimi et al. | |

FOREIGN PATENT DOCUMENTS

| | | |
|---|---|---|
| EP | 0657428 A1 | 6/1995 |
| EP | 1159964 A2 | 12/2001 |
| WO | WO 01/34593 | 5/2001 |

OTHER PUBLICATIONS

Vippagunta et al, 'Crystalline solids' Advanced Drug Delivery Reviews, vol. 48, p. 3-26, 2001.*
Bastin et al 'Salt Selection and Optimisation Procedures for Pharmaceutical New Chemical Entities' Organic Process Research and Development, vol. 4, p. 427-435, 2000.*
Supplementary European Search Report dated Jul. 22, 2010 in EP Application 08742733.2.2123 (PCT/US08/004640).
Liu, Y-L et al., "Ghrelin alleviates cancer chemotherapy-associated dyspepsia in rodents," Cancer Chemotherapy and Pharmacology, vol. 58, No. 3, pp. 326-333, Sep. 2006.
Rudd, John A. et al., "Anti-emetic activity of ghrelin in ferrets exposed to the cytotoxic anti-cancer agent cisplatin," Neuroscience Letters, vol. 392, No. 1-2, pp. 79-83, Jan. 9, 2006.
Paul, Bernhard J. et al., "A Practical Synthesis of the Pseudotripeptide RC-1291," Organic Process Research & Development, vol. 10, No. 2, pp. 339-345, 2006.
Yang, L., et al., "1-[2-(R)-(2-amino-2-methylpropionylamino)-3-(1H-indol-3-yl)propionyl]-3-benzylpiperidine-3(S)-carboxylic acid ethyl ester (L-163,540): a potent, orally bioavailable, and short-duration growth hormone secretagogue," Journal of Medicinal Chemistry, vol. 41, No. 14, pp. 2439-2441, Jul. 2, 1998.
Peeters et al., *Old and new targets for prokinetic drugs: motilin and ghrelin receptors*, Eu Rev Med Pharmacol Sci 2008: 12(Suppl 1): 136-137.
Cordido et al., *Ghrelin and Growth Hormone Secretagogues, Physiological and Pharmacological Aspect*, Current Drug Discovery Technologies, 2009, 6, 34-42.
Suchitra et al., *Relative efficacy of some prokinetic drugs in morphine-induced gastrointestinal transit delay in mice*, World J. Gastroenterol 2003;9(4): 779-783.
Ohno et al., *The Roles of Motilin and Ghrelin in Gastrointestinal Motility*, International Journal of Peptides, vol. 2010, Article ID 820794, 6 pages.
Aerssens et al., The rat lacks functional genes for motilin and for the motilin erceptor, Neurogastroenterology & Motility, vol. 16, p. 841 (2004).
Charoenthongtrakul et al., *Enhanced Gastrintestinal Motility with Orally Active Ghrelin Receptor Agonists*, The Journal of Pharmacology and Experimental Therapeutics 329:1178-1186 (2009).
Meerveld et al., *Preclinical studies of opioids and opioid antagonists on gastrointestinal function*, Neurogastroenterol Motil (2004) 16 (Suppl 2), 46-53).
De Winter, et al. "Effect of ghrelin and growth hormone-releasing peptide 6 on septic ileus in mice," *Neurogastroenterol Motil*, vol. 16, pp. 439-446 (2004).
Supplementary European Search Reported dated Jul. 23, 2010 in EP Application 05786631.1 (PCT/US2005/028851). Szarka, et al. "Methods for measurement of gastric motility," *Am J Physiol Gastrointest Liver Physiol*, vol. 296, pp. G461-G475 (2009).
Glilson, Sharon, Gastrointestinal motility disorders, About.com Guide Updated Jun. 8, 2006. Printed Sep. 24, 2010. http://heartburn.about.com/cs/causes/a/gastro_motility.htm.

* cited by examiner

*Primary Examiner* — Brandon Fetterolf
*Assistant Examiner* — Christopher R Stone
(74) *Attorney, Agent, or Firm* — Clark G. Sullivan; Arnall Golden Gregory LLP

(57) ABSTRACT

The present invention provides a method of stimulating the motility of the gastrointestinal system in a subject in need thereof, wherein the subject suffers from maladies (i.e., disorders, diseases, conditions, or drug- or surgery-induced dysfunction) of the gastrointestinal system, by administering to the subject a ghrelin mimetic, or pharmaceutically acceptable salt thereof. The invention also provides a method of treating a gastrointestinal malady by co-administering a ghrelin mimetic with a laxative, a $H_2$ receptor antagonist, a serotonin receptor agonist, pure or mixed, an antacid, an opioid antagonist, a proton pump inhibitor, a motilin receptor agonist, dopamine antagonist, a cholinergic agonist, a cholinesterase inhibitor, somatostatin, octreotide, or any combination thereof.

11 Claims, 16 Drawing Sheets

FIG 12A-D

METHOD OF STIMULATING THE MOTILITY OF THE GASTROINTESTINAL SYSTEM USING IPAMORELIN

RELATED APPLICATIONS

This application is a continuation-in-part of U.S. application Ser. No. 11/203,639, filed Aug. 12, 2005 which claims the benefit of U.S. Provisional Application 60/600,959, filed Aug. 12, 2004. This application also claims the benefit of U.S. Provisional Application 61/008,828, filed Dec. 21, 2007. The entire contents of each of the aforementioned applications is hereby incorporated by reference herein.

INCORPORATION BY REFERENCE

All references cited herein, including patents, patent applications, and published patent applications, are hereby incorporated by reference in their entireties, whether or not each is further individually incorporated by reference.

BACKGROUND OF THE INVENTION

Gastrointestinal (GI) motility is a coordinated neuromuscular process that transports nutrients through the digestive system. C. Scarpignato, "Pharmacological Stimulation of Gastrointestinal Motility Where We Are And Where Are We Going?" *Dig. Dis.*, 15: 112 (1997). Impaired (i.e., slowed) motility of the gastrointestinal system, which can be involved in gastroesophageal reflux disease, gastroparesis (e.g., diabetic and postsurgical), irritable bowel syndrome, ileus, and constipation (e.g., diet or opioid-induced), is one of the largest health care burdens of industrialized nations. S. D. Feighner et al., "Receptor for Motilin Identified in the Human Gastrointestinal System," *Science*, 284: 2184-2188 (Jun. 25, 1999).

Growth hormone secretagogues (GHS), such as ghrelin and mimetics thereof, have been reported to stimulate gastrointestinal motility. However, the specific GHS compounds that have been studied have pharmacokinetic properties that will not allow them to be used clinically for the treatment of gastrointestinal motility. Specifically, ghrelin is a 28-amino acid peptide that is produced in the stomach. The biologically active form of ghrelin, i.e., the acylated form, has a serum half-life of only 9-13 minutes (Akamizu et al. (2004) *European Journal of Endocrinology* 150:447-55). Additionally, synthetic GHS compounds such as GHRP-6 have been evaluated for the ability to treat GI motility. Similar to ghrelin, GHRP-6 has a short serum half life that prohibits the use of this compound from being used to treat GI motility disorders. Bowers et al. demonstrated that the serum half life of GHRP-6 is only 20 minutes ((1992) Journal of Clinical Endocrinology and Metabolism 74:292-8).

In view of the above, an effective, physiological way to effectively stimulate motility of the gastrointestinal system is highly desirable and would be an advance in the art.

SUMMARY OF THE INVENTION

The present invention relates to a method of stimulating the motility of the gastrointestinal system in a subject in need thereof, wherein the subject suffers from maladies (i.e., disorders, diseases, conditions, or drug- or surgery-induced dysfunction) of the gastrointestinal system. The method comprises administering to a subject in need thereof a therapeutically effective amount of a ghrelin mimetic compound or a pharmaceutically acceptable salt, hydrate or solvate thereof. In a preferred embodiment, the ghrelin mimetic is ipamorelin as represented by Formula I (see below), or a pharmaceutically acceptable salt, hydrate or solvate thereof.

As described above, ghrelin and ghrelin mimetic compounds have been shown to have limited serum half lives, and are therefore not suitable for use in treating GI motility disorders. In contrast to ghrelin and GHRP-6, the serum half life of ipamorelin in humans has been demonstrated to be between 3 and 6.5 hours. Accordingly, the instant invention provides methods and therapeutically effective compositions for stimulating the motility of the gastrointestinal system.

Stimulation of gastrointestinal motility is used in a method of treating opioid-induced gastrointestinal dysfunction, e.g., morphine-induced bowel dysfunction or constipation, in a subject in need thereof comprising administering a therapeutically effective amount of a ghrelin mimetic compound or a pharmaceutically acceptable salt, hydrate or solvate thereof. The subject may be using opiates or opioids for post-surgical pain management or for chronic pain management. Exemplary opiates and opioids include morphine, codeine, oxycodone, hydromorphone, hydrocodone, methadone, fentanyl, and combinations with anti-inflammatory agents such as acetaminophen or aspirin. A preferred ghrelin mimetic is ipamorelin as represented by Formula I, or a pharmaceutically acceptable salt, hydrate or solvate thereof.

Stimulation of gastrointestinal motility can be used to treat gastroparesis in a subject in need thereof by administering a therapeutically effective amount of a ghrelin mimetic compound. A preferred ghrelin mimetic is ipamorelin as represented by Formula I, or a pharmaceutically acceptable salt, hydrate, derivative, acid amide, or solvate thereof.

In a further embodiment, stimulation of gastrointestinal motility is used in a method of treating gastroesophageal reflux disease (GERD) in a subject in need thereof comprising administering a therapeutically effective amount of a ghrelin mimetic compound. In a particular embodiment, the ghrelin mimetic is ipamorelin as represented by Formula I, or a pharmaceutically acceptable salt, hydrate or solvate thereof. In a particular embodiment, the gastroesophageal reflux disease is nocturnal gastroesophageal reflux disease.

The invention also provides methods for stimulating gastrointestinal motility for the treatment of irritable bowel syndrome (IBS) in a subject in need thereof by administering a therapeutically effective amount of a ghrelin mimetic compound. A preferred ghrelin mimetic is ipamorelin as represented by Formula I, or a pharmaceutically acceptable salt, hydrate or solvate thereof. The irritable bowel syndrome can be constipation-predominant irritable bowel syndrome or alternating constipation/diarrhea irritable bowel syndrome.

The invention also provides methods for stimulating gastrointestinal motility to treat constipation in a subject in need thereof by administering a therapeutically effective amount of a ghrelin mimetic compound. A preferred ghrelin mimetic is ipamorelin as represented by Formula I, or a pharmaceutically acceptable salt, hydrate or solvate thereof.

In one embodiment, stimulation of gastrointestinal motility is used in a method of treating surgery-induced or related gastrointestinal dysfunction, e.g. post-operative ileus, in a subject in need thereof comprising administering a therapeutically effective amount of a ghrelin mimetic compound. In a particular embodiment, the ghrelin mimetic is ipamorelin as represented by Formula I, or a pharmaceutically acceptable salt, hydrate or solvate thereof.

A preferred ghrelin mimetic is ipamorelin as represented by Formula I (α-Methylalanine-L-histidine-D-β-(2-naphthyl)-alanine-D-phenylalanine-L-lysinamide or H-Aib-His-β-(2-naphthyl)-D-Ala-D-Phe-Lys-NH$_2$):

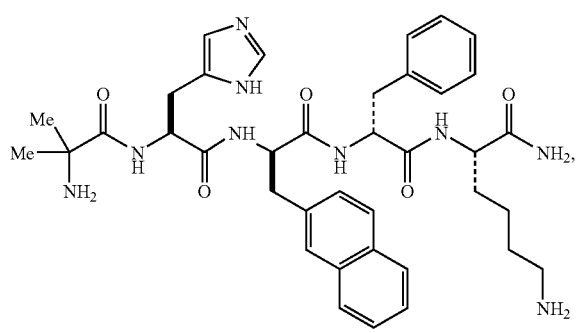

or a pharmaceutically acceptable salt, hydrate or solvate thereof.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following Detailed Description, given by way of example, but not intended to limit the invention solely to the specific embodiments described, may best be understood in conjunction with the accompanying drawings, in which.

DETAILED DESCRIPTION

Figure 1:
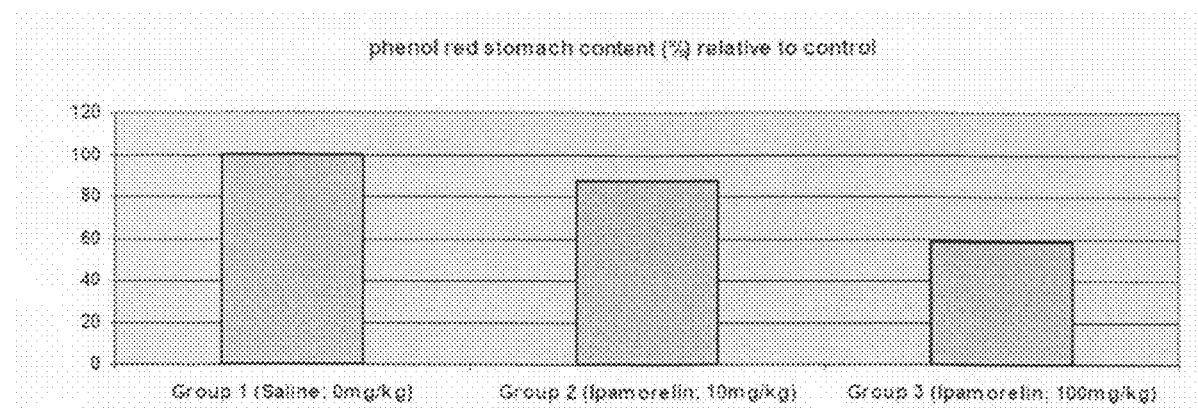
FIG. 1 shows the gastrokinetic efficacy of oral administration of ipamorelin at 10 and 100 mg/kg in a rat model for post-operative ileus.

The present invention relates to a method of stimulating the motility of the gastrointestinal system in a subject in need thereof, wherein the subject suffers from maladies (i.e., disorders or diseases or drug- or surgery-induced dysfunction) of the gastrointestinal system. In certain embodiments, the maladies include opioid-induced gastrointestinal dysfunction, e.g., morphine-induced gastrointestinal dysfunction, constipation, diabetes-related gastroparesis, gastroesophageal reflux disease (GERD), irritable bowel syndrome (IBS), or drug- or surgery-induced gastrointestinal dysfunction, e.g., post-operative ileus. The method comprises administering to a subject in need thereof a therapeutically effective amount of a ghrelin mimetic compound or a pharmaceutically acceptable salt, hydrate or solvate thereof. The ghrelin mimetic is preferably ipamorelin as represented by Formula I, or a pharmaceutically acceptable salt, hydrate or solvate thereof.

Ghrelin Mimetics

As used herein, the terms "ghrelin mimetic" or "ghrelin mimetic compound" or "ghrelin agonist" are synonymous with the historical terms "growth hormone secretagogue," or "growth hormone secretagogue compound". A ghrelin mimetic or ghrelin agonist refers to a substance (e.g., a molecule, a compound) which promotes (induces or enhances) at least one function that is characteristic of binding to the ghrelin receptor (GRLN). The GRLN receptor has been previously reported in the literature as the $GHS_{1a}$ receptor which reflected its first known attribute—secretion of growth hormone. The ghrelin receptor is primarily expressed in the hypothalamus and pituitary. Activation of these receptors in the pituitary induces the secretion of growth hormone. In addition to inducing the secretion of growth hormone, recent studies have shown the ghrelin mimetics can increase appetite and body weight. In a particular embodiment, the ghrelin mimetics are those described in U.S. Pat. Nos. 5,767,085, 6,303,620, 6,576,648, 5,977,178, 6,566,337, 6,083,908, 6,274,584 and 6,919,315, the entire content of all of which are incorporated herein by reference.

Subsequently the GRLN receptor was identified in locations in the body other than the pituitary and hypothalamus, such as the gastrointestinal tract and the vasculature. The binding of ghrelin or ghrelin mimetics to these receptors resulted in pharmacological activity other than, or in addition to, growth hormone release. Specifically, this other pharmacologic activity was an increase in gastrointestinal prokinetic activity as well as changes in cardiac function. Thus, the growth hormone secretagogue compounds as they were previously named are now more generally called ghrelin mimetics or agonists to represent the wider spectrum of physiological actions resulting from binding to its receptor (GRLN).

Most identified ghrelin mimetics have a core peptide backbone with differing lengths of the backbone (tri-, tetra-, penta-, and hexapeptides, as well as macrocyclic). It is also expected that the different molecular structures will result in differing affinities for the ghrelin receptor and, therefore, could produce differing pharmacological outcomes. A priori one cannot determine which molecule might produce unusual activity or potency relative to others in a general class. It generally emerges from scientific investigation with an unusual result or finding.

A compound having GRLN receptor agonist activity can be identified and activity assessed by any suitable method. For example, the binding affinity of a GRLN receptor agonist to the GRLN receptor can be determined employing receptor binding assays and growth hormone stimulation can be assessed as described in U.S. Pat. No. 6,919,315, which is incorporated herein by reference. The ghrelin mimetics can be obtained from any source, including any commercial source.

In the case of this invention the preferred ghrelin mimetic is ipamorelin as represented by the structural Formula I (α-Methylalanine-L-histidine-D-β-(2-naphthyl)-alanine-D-phenylalanine-L-lysinamide or H-Aib-His-β-(2-naphthyl)-D-Ala-D-Phe-Lys-NH$_2$):

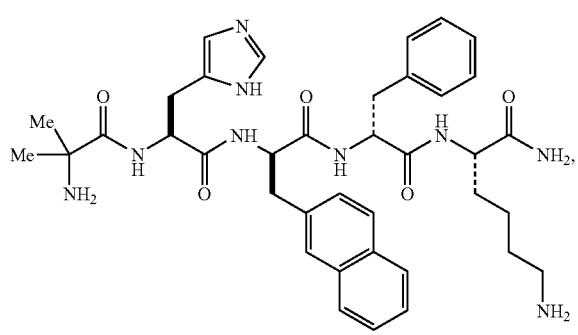

or a pharmaceutically acceptable salt, hydrate, acid, amide, crystal or solvate thereof.

The present invention is based in part on the surprising discovery made by the present inventors that certain particular ghrelin mimetics, in particular, ipamorelin, have a surprisingly efficacious and potent stimulatory effect on gastrointestinal motility. Although ipamorelin is a potent growth hormone secretagogue, its binding affinity with the GRLN receptor is about 2-3 logs weaker than many other reported ghrelin mimetics.

Co-Administered Substances

Another aspect of the present invention relates to the co-administration of one or more substances and a ghrelin mimetic, e.g., ipamorelin, to treat a gastrointestinal disorder, disease, or condition. Co-administered can mean the administration of two or more substances together as a single pharmaceutical composition, or the administration of two or more substances in a short period of time, e.g., within seconds of each other to within a day of each other.

Peripherally Acting Opioid Antagonists

It is possible to administer peripherally acting opioid receptor antagonists, such as, for example, methylnaltrexone, naloxone, naltrexone, nalmefene and alvimopan (ENTEREG™), which do not cross the blood-brain barrier, to treat opioid-induced side effects without provoking opioid withdrawal symptoms or reverse analgesia. (Holzer P., "Opioids and Opioid Receptors in the Enteric Nervous System: From a Problem in Opioid Analgesia to a Possible New Prokinetic Therapy in Humans," Neurosci Lett., 361(1-3): 192-5 (2004), incorporated herein by reference). As used herein, peripherally acting opioid antagonists refer to opioid antagonists that act peripherally (i.e., not centrally, for example, do not act on the central nervous system).

Proton Pump Inhibitors

In another aspect, the present invention provides for co-administration of a ghrelin mimetic, e.g., ipamorelin, and a proton pump inhibitor for the treatment of gastrointestinal conditions or maladies. Proton pump inhibitors suppress gastric acid secretion, the final step of acid production, by specific inhibition of the H$^+$K$^+$-ATPase enzyme system at the secretory surface of gastric parietal cells. Proton pump inhibitors include benzimidazole compounds, for example, esomeprazole (NEXIUM®), omeprazole (PRILOSEC™), lansoprazole (PREVACID™), rabeprazole (ACIPHEX™). and pantoprazole (Protonix™). These proton pump inhibitors contain a sulfinyl group situated between substituted benzimidazole and pyridine rings. At neutral pH, esomeprazole, omeprazole, lansoprazole, and pantoprazole are chemically stable, lipid soluble, weak bases that are devoid of inhibitory activity. These uncharged weak bases reach parietal cells from the blood and diffuse into the secretory canaliculi, where the drugs become protonated and thereby trapped. The protonated species rearranges to form a sulfenic acid and a sulfenamide, the latter species capable of interacting with sulfhydryl groups of H$^+$K$^+$-ATPase. Full inhibition occurs with two molecules of inhibitor per molecule of enzyme. The specificity of the effects of proton pump inhibitors is believed to derive from: a) the selective distribution of H$^+$K$^+$-ATPase; b) the requirement for acidic conditions to catalyze generation of the reactive inhibitor; and c) the trapping of the protonated drug and the cationic sulfenamide within the acidic canaliculi and adjacent to the target enzyme. Goodman & Gilman's The Pharmacological Basis of Therapeutics, 9th Edition, pp. 901-915 (1996), incorporated herein by reference.

H$_2$ Receptor Antagonists

In yet another aspect, the present invention provides for the co-administration of a ghrelin mimetic, e.g., ipamorelin, and an H$_2$ receptor antagonist for the treatment of gastrointestinal conditions or maladies. H$_2$ receptor antagonists competitively inhibit the interaction of histamine with H$_2$ receptors. They are highly selective and have little or no effect on H$_1$ receptors. Although $H_2$ receptors are present in numerous tissues, including vascular and bronchial smooth muscle, $H_2$ receptor antagonists interfere remarkably little with physiological functions other than gastric acid secretion. $H_2$ receptor antagonists include, but are not limited to, nizatidine (AXID™), ranitidine (ZANTAC™ and TRITEC™), famotidine (PEPCID AC™), and cimetidine (TAGAMET™. Goodman & Gilman's The Pharmacological Basis of Therapeutics, 9th Edition, pp. 901-915 (1996), incorporated herein by reference. $H_2$ receptor antagonists inhibit gastric acid secretion elicited by histamine, other $H_2$ agonists, gastrin, and, to a lesser extent, muscarinic agonists. $H_2$ receptor antagonists also inhibit basal and nocturnal acid secretion.

Antacids

Another aspect of the present invention provides a method for the co-administration of a ghrelin mimetic, e.g., ipamorelin, and an antacid for treating a gastrointestinal condition or malady. For example, compounds of the invention can be co-administered with antacids to neutralize gastric acid. For instance, aluminum and magnesium hydroxide (MAALOX™ and MYLANTA™) neutralize gastric acidity, resulting in an increase in pH in the stomach and duodenal bulb.

Laxatives

The present invention further provides a method for the co-administration of a ghrelin mimetic, e.g., ipamorelin, and a laxative for treating a gastrointestinal condition or malady. Laxatives come in various forms, including, for example, liquids, tablets, suppositories, powders, granules, capsules, chewing gum, chocolate-flavored wafers, and caramels. The basic types of laxatives are bulk-forming laxatives, lubricant laxatives, stool softeners (also called emollient laxatives), and stimulant laxatives.

Bulk-forming laxatives contain materials, such as cellulose and psyllium, that pass through the digestive tract without being digested. In the intestines, these materials absorb liquid and swell, making the stool soft, bulky, and easier to pass. The bulky stool then stimulates the bowel to move. Laxatives in this group include such brands as FIBERCON®, FIBERALL®, and METAMUCIL®.

Lubricant laxatives include, for example, mineral oil. Mineral oil is the most widely used lubricant laxative. Taken by mouth, the oil coats the stool. This keeps the stool moist and soft and makes it easier to pass. Lubricant laxatives are often used for patients who need to avoid straining (e.g., after abdominal surgery).

Stool softeners (emollient laxatives) make stools softer and easier to pass by increasing their moisture content. This type of laxative does not really stimulate bowel movements, but it makes it possible to have bowel movements without straining. Stool softeners are best used to prevent constipation in people who need to avoid straining, because of recent surgery, for example. Stool-softening agents include, for example, docusate sodium (COLACE®, REGUTOL®, and others), docusate calcium (SURFAK®, DC SOFTGELS®) and docusate potassium (DIALOSE®, DIOCTO-K®).

Serotonin Receptor (5-HT) Agonists (Pure or Mixed)

The present invention also provides a method for the co-administration of a ghrelin mimetic, e.g., ipamorelin, and a serotonin receptor agonist, such as a 5-HT$_4$ agonist, for treating a gastrointestinal condition or malady. The serotonin agonists can either be a pure or mixed 5-HT receptor subtype(s), or mixed with other central nervous system receptors such as dopamine.

The 5-HT$_4$ agonists speed up movement of bowel contents through the colon and reduce sensitivity to intestinal nerve stimulation. Suitable serotonin agonists which can be used in combination with the compounds of the invention include, but not restricted to, rauwolscine, yohimbine, metoclopramide, prucalopride and tegaserod (ZELNORM®). Spiller R., "Serotonergic Modulating Drugs for Functional Gastrointestinal Diseases," *Br J Clin Pharmacol.* 54:11-20 (2002) and U.S. Pat. No. 6,413,988, incorporated herein by reference.

Motilin Receptor Agonists

The present invention further provides a method for the co-administration of a ghrelin mimetic, e.g., ipamorelin, and a motilin receptor agonist for treating a gastrointestinal condition or malady. Motilin is a peptide of 22 amino acids which is produced in the gastrointestinal system of a number of species. Motilin induces smooth muscle contractions in the stomach tissue of dogs, rabbits, and humans as well as in the colon of rabbits. Apart from local gastrointestinal intestinal tissues, motilin and its receptors have been found in other tissues.

In addition to motilin, there are other substances which are agonists of the motilin receptor and which elicit gastrointestinal emptying. One of those agents is the antibiotic erythromycin. Studies have shown that erythromycin elicits biological responses that are comparable to motilin itself and therefore can be useful in the treatment of diseases such as chronic idiopathic intestinal pseudo-obstruction and gastroparesis. Weber, F. et al., *The American Journal of Gastroenterology*, 88:4, 485-90 (1993), incorporated herein by reference.

Dopamine Antagonists

Another aspect of the present invention provides a method for the co-administration of a ghrelin mimetic, e.g., ipamorelin, and a dopamine antagonist for treating a gastrointestinal condition or malady.

Dopamine antagonists are drugs that bind to, but do not activate, dopamine receptors thereby blocking the actions of dopamine or exogenous agonists. This class of drugs includes, but is not limited to, metoclopramide, domperidone, amisulpride, clebopride, mosapramine, nemonapride, remoxipride, risperidone, sulpiride, sultopride and ziprasidone.

Cholinesterase Inhibitors

The present invention also provides a method for the co-administration of a ghrelin mimetic, e.g., ipamorelin, and a cholinesterase inhibitor for treating a gastrointestinal condition or malady. The term "cholinesterase inhibitor" refers to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and physostigmine, ambenonium chloride (MYTELASE®), edrophonium chloride (TENSILON®), neostigmine (PROSTIGMINE®), piridogstimina (MESTINON®), distigmine bromide, eptastigmine, galanthamine, axeclidine, acetylcholine bromine, acetylcholine chloride, aclatonium napadisilate, benzpyrinium bromide, carbachol, carponium chloride, cemecarium bromide, dexpanthenol, diisopropyl paraoxon, echothiophate chloride, eseridine, furtrethonium, methacholine chloride, muscarine, oxapropanium idoide, and xanomeline.

Stereochemistry

Many of the compounds described herein can have one or more chiral centers and therefore can exist in different enantiomeric forms. If desired, a chiral carbon can be designated with an asterisk (*). When bonds to the chiral carbon are depicted as straight lines in the formulas of the invention, it is understood that both the (R) and (S) configurations of the chiral carbon, and hence both enantiomers and mixtures thereof are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When a compound of the present invention has two or more chiral carbons, it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers which are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

Screening

It is understood that ghrelin mimetic compounds can be identified, for example, by screening libraries or collections of molecules using suitable methods. Another source for the compounds of interest are combinatorial libraries which can comprise many structurally distinct molecular species. Combinatorial libraries can be used to identify lead compounds or to optimize a previously identified lead. Such libraries can be manufactured by well-known methods of combinatorial chemistry and screened by suitable methods.

Methods of Treating Gastrointestinal Maladies

The present invention provides a method of stimulating the motility of the gastrointestinal system in a subject in need thereof, wherein the subject suffers from maladies (i.e., disorders, diseases, conditions, or drug- or surgery-induced dysfunction) of the gastrointestinal system. The method comprises administering to a subject in need thereof a therapeutically effective amount of a ghrelin mimetic compound or a pharmaceutically acceptable salt, hydrate or solvate thereof. The ghrelin mimetic is ipamorelin as represented by Formula I, or a pharmaceutically acceptable salt, hydrate or solvate thereof.

As used herein, the term "gastrointestinal maladies" refers to any disease, disorder, condition, or dysfunction resulting in impaired gastrointestinal function. For example, the gastrointestinal malady can be opioid-induced gastrointestinal dysfunction, e.g., morphine-induced constipation, post-operative ileus, or gastroparesis.

Constipation

In another aspect, the invention provides a method of treating constipation by administering a therapeutically effective amount of a ghrelin mimetic, e.g., ipamorelin. Constipation is a condition in which a person has uncomfortable or infrequent bowel movements. A person with constipation produces hard stools that can be difficult to pass. The person also can feel as though the rectum has not been completely emptied. Acute constipation begins suddenly and noticeably. Chronic constipation, on the other hand, can begin insidiously and persist for months or years.

The method of treating constipation of the invention can further comprise co-administering a ghrelin mimetic, e.g., ipamorelin, with a therapeutically effective amount of a laxative. Suitable laxatives include, but are not limited to, bulk forming laxatives, lubricant laxatives, stool softeners, or any combination thereof.

Opioid-Induced Constipation

The invention provides a method of treating opioid-induced constipation by administering a therapeutically effective amount of a ghrelin mimetic, e.g., ipamorelin. Use of opioid analgesics to relieve chronic pain can cause effects on organs outside the targets in the central nervous system. For example, opioid action can slow stomach emptying and inhibit bowel movement. The increased time of fecal contents in the intestines results in excessive absorption of water and sodium from fecal contents, resulting in harder, drier stools and constipation. This effect afflicts approximately 90% of individuals on analgesic pain killers. For chronic pain patients on opioid medications, the resulting constipation can be a dose limiting side-effect. In addition, analgesics used for post-surgical pain management can cause opioid-induced constipation. Suitable opioids include, but are not limited to, morphine, codeine, oxycodone, hydromorphone, hydrocodone, methadone, fentanyl, and combinations with anti-inflammatory agents such as acetaminophen or aspirin or any combination thereof.

The method of treating opioid-induced constipation can further comprise co-administering a ghrelin mimetic compound, e.g., ipamorelin, with a therapeutically effective amount of a peripherally acting opioid antagonist, a laxative, or any combination thereof. Suitable peripherally acting opioid antagonists include, but are not limited to, methylnaltrexone, naltrexone, nalmefene, naloxone and alvimopan or any combination thereof. Suitable laxatives include, but are not limited to bulk forming laxatives, lubricant laxatives, stool softeners, or any combination thereof.

Post-operative ileus

The present invention provides a method of treating post-operative ileus by administering a therapeutically effective amount of a ghrelin mimetic, e.g., ipamorelin. It is well established that the motility of the gastrointestinal (GI) tract is temporarily impaired after surgery. The effect that an abdominal operation has on gastrointestinal motility is generally referred to as "post-operative ileus," a term denoting disruption of the normal coordinated movements of the gut, resulting in failure of the propulsion of intestinal contents. Ileus has also been defined as a functional, non-mechanical obstruction of the bowel. The term "post-operative ileus" refers to delay in normal gastric and colonic emptying.

The method of treating post-operative ileus can further comprise co-administering a ghrelin mimetic, e.g., ipamorelin, with a therapeutically effective amount of a dopamine antagonist. Suitable dopamine antagonists include, but are not limited to, metoclopramide, domperidone, amisulpride, clebopride, mosapramine, nemonapride, remoxipride, risperidone, sulpiride, sultopride and ziprasidone, or any combination thereof.

Irritable Bowel Syndrome

The present invention provides a method of treating irritable bowel syndrome by administering a therapeutically effective amount of a ghrelin mimetic, e.g., ipamorelin. Irritable bowel syndrome (IBS) is a functional disorder effecting motility of the entire gastrointestinal tract that can produce abdominal pain, constipation, and/or diarrhea. The impaired movement of the digestive tract in IBS is not accompanied by a change in physical structure, such as inflammation or tumors. The symptoms of IBS are thought to be related to abnormal muscle contractions in any part of the intestines.

In this syndrome, the gastrointestinal tract is especially sensitive to gastrointestinal stimuli. Stress, diet, drugs, hormones, or minor irritants can cause the gastrointestinal tract to contract abnormally. There are different types of IBS: constipation-predominant, diarrhea-predominant and alternating constipation-predominant/diarrhea-predominant IBS.

The method of treating IBS may comprise co-administering a ghrelin mimetic compound, e.g., ipamorelin, with a therapeutically effective amount of $H_2$ receptor antagonist; a serotonin 5-HT agonist; a laxative; or any combination thereof.

Suitable $H_2$ receptor antagonists include, but are not limited to, nizatidine, ranitidine, famotidine, and cimetidine, or any combination thereof. Suitable central nervous system receptor agonists include, but are not limited to, rauwolscine, yohimbine, metoclopramide, tegaserod, or any combination thereof. Suitable laxatives include, but are not limited to, bulk forming laxatives, lubricant laxatives, stool softeners, or any combination thereof.

Gastroesophageal Reflux Disorder

The invention further provides a method of treating gastroesophageal reflux disorder by administering a therapeutically effective amount of a ghrelin mimetic, e.g., ipamorelin. Gastroesophageal reflux disease (GERD) is a condition in which gastric stomach contents (e.g., bile salts) back up into the food pipe (esophagus), causing chronic regurgitation of gastric contents from the stomach into the lower esophagus. Commonly known as heartburn, GERD causes esophageal irritation and inflammation.

For people with GERD, the esophageal sphincter (a ring-shaped muscle located at the lower end of the esophagus to prevent stomach contents from going backwards into the esophagus) can fail to carry out its protective duties. Instead of opening only when a person is eating or swallowing, it relaxes and allows digestive juices to reflux into the esophagus and irritate the esophageal lining.

Two types of GERD have been identified, upright or daytime GERD and supine or nocturnal GERD. Nocturnal reflux episodes occur less frequently, but acid clearance is more prolonged. Nocturnal reflux can be associated with the complications of GERD, such as esophageal erosions, ulceration, and respiratory symptoms. An estimated 17 million Americans currently suffer from heartburn and other symptoms of GERD.

The method of treating GERD comprises co-administering a ghrelin mimetic compound, e.g., ipamorelin, with a therapeutically effective amount of $H_2$ receptor antagonist; an antacid; a proton pump inhibitor; or any combination thereof.

Suitable $H_2$ receptor antagonist include, but are not limited to, nizatidine, ranitidine, famotidine, and cimetidine, or any combination thereof. Suitable antacids include, but are not limited to, aluminum and magnesium hydroxide and combinations thereof. Suitable proton pump inhibitors include, but are not limited to, esomeprazole (NEXIUM®), omeprazole, lansoprazole, pantoprazole, or a combination thereof.

Gastroparesis

The present invention provides a method of treating gastroparesis, e.g. diabetic or idiopathic, by administering a therapeutically effective amount of a ghrelin mimetic, e.g., ipamorelin. Gastroparesis, also referred to as delayed gastric emptying, is a disorder in which the stomach takes too long to empty its contents. It often occurs in people with type 1 diabetes mellitus or type 2 diabetes mellitus. Gastroparesis can occur when nerves to the stomach are damaged or stop working. The vagus nerve controls the movement of food through the digestive tract. If the vagus nerve is damaged, the muscles of the stomach and intestines do not work normally, and the movement of food is slowed or stopped. Diabetes can damage the vagus nerve if blood glucose levels remain high over a long period of time. High blood glucose causes chemical changes in nerves and damages the blood vessels that carry oxygen and nutrients to the nerves.

The method of treating gastroparesis can comprise co-administering a ghrelin mimetic compound, e.g., ipamorelin, with a therapeutically effective amount of dopamine antagonist. Suitable dopamine antagonists include, but are not limited to, metoclopramide, domperidone, amisulpride, clebopride, mosapramine, nemonapride, remoxipride, risperidone, sulpiride, sultopride and ziprasidone, or any combination thereof.

The invention further relates to pharmaceutical compositions useful for stimulating (i.e., inducing) motility of the gastrointestinal system. The pharmaceutical composition comprises a ghrelin mimetic and optionally a pharmaceutically acceptable carrier. The pharmaceutical composition can comprise a second amount of a suitable therapeutic agent. A suitable therapeutic agent can be determined based on the condition being treated in the subject.

For example, the pharmaceutical composition can comprise a first amount of a ghrelin mimetic, e.g., ipamorelin, and a second amount of a laxative when treating constipation. The pharmaceutical composition of the present invention can optionally contain a pharmaceutically acceptable carrier. The ghrelin mimetic and laxative can each be present in the pharmaceutical composition in a therapeutically effective amount. In another aspect, said first and second amount can together comprise a therapeutically effective amount.

The pharmaceutical composition can comprise a first amount of a ghrelin mimetic and a second amount of a $H_2$ receptor antagonist. The pharmaceutical composition of the present invention can optionally contain a pharmaceutically acceptable carrier. The ghrelin mimetic and $H_2$ receptor antagonist can each be present in the pharmaceutical composition in a therapeutically effective amount. In another aspect, said first and second amount can together comprise a therapeutically effective amount.

The pharmaceutical composition can comprise a first amount of a ghrelin mimetic and a second amount of a serotonin receptor agonist. The pharmaceutical composition can optionally contain a pharmaceutically acceptable carrier. The ghrelin mimetic and serotonin receptor agonist can each be present in the pharmaceutical composition in a therapeutically effective amount. The first and second amount can together comprise a therapeutically effective amount.

The pharmaceutical composition can comprise a first amount of a ghrelin mimetic, e.g., ipamorelin, and a second amount of an antacid. The pharmaceutical composition can optionally contain a pharmaceutically acceptable carrier. The ghrelin mimetic and antacid can each be present in the pharmaceutical composition in a therapeutically effective amount. In another aspect, said first and second amount can together comprise a therapeutically effective amount.

The pharmaceutical composition can comprise a first amount of a ghrelin mimetic and a second amount of an opioid antagonist. The pharmaceutical composition can optionally contain a pharmaceutically acceptable carrier. The ghrelin mimetic and opioid antagonist can each be present in the pharmaceutical composition in a therapeutically effective amount. The first and second amount can together comprise a therapeutically effective amount.

The pharmaceutical composition can comprise a first amount of a ghrelin mimetic and a second amount of a proton pump inhibitor. The pharmaceutical composition can optionally contain a pharmaceutically acceptable carrier. The ghrelin mimetic and proton pump inhibitor can each be present in the pharmaceutical composition in a therapeutically effective amount. The first and second amount can together comprise a therapeutically effective amount.

The pharmaceutical composition can comprise a first amount of a ghrelin mimetic and a second amount of a motilin receptor agonist. The pharmaceutical composition can optionally contain a pharmaceutically acceptable carrier. The ghrelin mimetic and motilin receptor agonist can each be present in the pharmaceutical composition in a therapeutically effective amount. The first and second amount can together comprise a therapeutically effective amount.

The pharmaceutical composition can comprise a first amount of a ghrelin mimetic and a second amount of a dopamine antagonist. The pharmaceutical can optionally contain a pharmaceutically acceptable carrier. The ghrelin mimetic and dopamine antagonist can each be present in the pharmaceutical composition in a therapeutically effective amount. The first and second amount can together comprise a therapeutically effective amount.

The pharmaceutical composition can comprise a first amount of a ghrelin mimetic and a second amount of a cholinesterase inhibitor. The pharmaceutical composition can optionally contain a pharmaceutically acceptable carrier. The ghrelin mimetic and cholinesterase inhibitor can each be present in the pharmaceutical composition in a therapeutically effective amount. The first and second amount can together comprise a therapeutically effective amount.

The pharmaceutical composition can comprise a first amount of a ghrelin mimetic and a second amount of somatostatin. The pharmaceutical composition can optionally contain a pharmaceutically acceptable carrier. The ghrelin mimetic and somatostatin can each be present in the pharmaceutical composition in a therapeutically effective amount. The first and second amount can together comprise a therapeutically effective amount.

The invention further relates to use of a ghrelin mimetic compound for the manufacture of a medicament for stimulating (i.e., inducing) the motility of the gastrointestinal system.

Subject, as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species. In a preferred embodiment, the mammal is a human.

As used herein, treating and treatment refer to stimulating (e.g., inducing) motility of the gastrointestinal system.

As used herein, therapeutically effective amount refers to an amount sufficient to elicit the desired biological response. The desired biological response is stimulating (e.g., inducing) motility of the gastrointestinal system. The desired biological response is stimulating (e.g., inducing) motility of the gastrointestinal system to treat opioid induced constipation in a subject in need thereof. The subject may be using opioids for post-surgical pain management or for chronic pain management.

The desired biological response is stimulating (e.g., inducing) motility of the gastrointestinal system to treat gastroparesis in a subject in need thereof.

The desired biological response is stimulating (e.g., inducing) motility of the gastrointestinal system to treat gastroesophageal reflux disease in a subject in need thereof. The gastroesophageal reflux disease is nocturnal gastroesophageal reflux disease.

The desired biological response is stimulating (e.g., inducing) motility of the gastrointestinal system to treat irritable bowel syndrome in a subject in need thereof. The irritable bowel syndrome is constipation-predominant irritable bowel syndrome. In yet another embodiment, the irritable bowel syndrome is constipation/diarrhea irritable bowel syndrome.

The desired biological response is stimulating (e.g., inducing) motility of the gastrointestinal system to treat constipation in a subject in need thereof.

The desired biological response is stimulating (e.g., inducing) motility of the gastrointestinal system to treat post-operative ileus in a subject in need thereof.

Pharmaceutical Compositions

Pharmaceutical compositions suitable for use in the present invention include compositions wherein the active ingredients are contained in a therapeutically effective amount to achieve its intended purpose. It will be appreciated that the unit content of active ingredient or ingredients contained in an individual dose of each dosage form need not in itself constitute an effective amount since the necessary effective amount can be reached by administration of a plurality of dosage units (such as capsules or tablets or vials or combinations thereof). In addition, it is understood that at some dosage levels, an effective amount may not show any measurable effect until after a week, a month, three months, or six months of usage. Determination of the effective amounts is well within the capability of those skilled in the art, especially in light of the detailed disclosure provided herein. The specific dose level for any particular user will depend upon a variety of factors including the age, the physical activity level, general health, and the severity of the gastrointestinal malady.

A therapeutically effective dose also refers to that amount necessary to achieve the desired effect without unwanted or intolerable side effects. Toxicity and therapeutic efficacy of a ghrelin mimetic, e.g., ipamorelin, of the invention can be determined by standard pharmaceutical procedures in cell cultures or experimental animals. Using standard methods, the dosage that shows effectiveness in about 50% of the test population, the $ED_{50}$, may be determined. Similarly, the dosage that produces an undesirable side effect to 50% of the population, the $SD_{50}$, can be determined. The dose ratio between side effect and therapeutic effects can be expressed as the therapeutic index and it can be expressed as a ratio between $SD_{50}/ED_{50}$ Ghrelin mimetics with high therapeutic indexes are preferred, e.g., ipamorelin, i.e., those which are effective at low dosage and which do not have undesirable side effects, if any, until very high doses. A preferred therapeutic index is greater than about 3, more preferably, the therapeutic index is greater than 10, most preferably the therapeutic index is greater than 25, such as, for example, greater than 50. Furthermore, ghrelin mimetics that do not have side effects at any dosage levels are more preferred. Finally, ghrelin mimetics that are effective at low dosages and do not have side effects at any dosage levels are most preferred. The exact formulation, route of administration and dosage can be chosen depending on the desired effect and can be made by those of skill in the art.

In certain embodiments, the ghrelin mimetics are formulated as pharmaceutically acceptable salts. As used herein, the term pharmaceutically acceptable salt refers to a salt of a compound to be administered prepared from pharmaceutically acceptable non-toxic acids including inorganic acids, organic acids, solvates, hydrates, or clathrates thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

The ghrelin mimetics of the invention can be prepared in the form of their hydrates, such as hemihydrate, monohydrate, dihydrate, trihydrate, tetrahydrate and the like and as solvates.

The ghrelin mimetics, e.g., ipamorelin, and derivatives thereof and any co-administered agents can be incorporated into any suitable pharmaceutical compositions which may be appropriate or suitable for administration. Such compositions typically comprise an active agent (e.g., a ghrelin mimetic of the invention) and a pharmaceutically acceptable carrier.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the pharmaceutical compositions of the invention. Modifications can be made to any of the pharmaceutical composition components to affect solubility or clearance of the factors of the invention. Peptidic molecules may also be synthesized with D-amino acids to increase resistance to enzymatic degradation. In some cases, the composition can be co-administered with one or more solubilizing agents, preservatives, and permeation enhancing agents.

Administration of Ghrelin Mimetics

The therapeutically effective amount or dose will depend on the age, sex and weight of the patient, and the current medical condition of the patient. The skilled artisan will be able to determine appropriate dosages depending on these and other factors to achieve the desired biological response.

A suitable dose per day for a ghrelin mimetic of the invention can be in the range of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 0.300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg.

Other suitable doses per day for a ghrelin mimetic of the invention include doses of about or greater than 1 ng, about 5 ng, about 10 ng, about 20 ng, about 30 ng, about 40 ng, about 50 ng, about 100 ng, about 200 ng, about 300 ng, about 400 ng, about 500 ng, about 1 µg, about 5 µg, about 10 µg, about 20 µg, about 30 µg, about 40 µg, about 50 µg, about 100 µg, about 200 µg, about 300 µg, about 400 µg, about 500 µg (0.5 mg), about 1 mg, about 1.25 mg, about 1.5 mg, about 2.0 mg, about 2.5 mg, about 3.0 mg, about 3.5 mg, about 4.0 mg, about 4.5 mg, about 5 mg, about 10 mg, about 20 mg, about 30 mg, about 40 mg, about 50 mg, about 100 mg, about 200 mg, about 300 mg, about 400 mg, about 500 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 3,000 mg, about 3,500 mg, about 4,000 mg, about 4,500 mg, about 5,000 mg, about 5,500 mg, about 6,000 mg, about 6,500 mg, about 7,000 mg, about 7,500 mg, about 8,000 mg, about 8,500 mg, about 9,000 mg, or about 9,500 mg.

A suitable dose of the ghrelin mimetic can be in the range of from about 0.20 mg to about 4000 mg per day, such as from about 1 mg to about 4000 mg, for example, from about 5 mg to about 3000 mg, such as about 10 mg to about 2400 mg per day. The dose can be administered in a single dosage or in multiple dosages, for example from 1 to 4 or more times per day. When multiple dosages are used, the amount of each dosage can be the same or different.

A suitable dose for an additional therapeutic agent, such as, for example, a laxative, can be in same range as described above for the ghrelin mimetic. The dose of ghrelin mimetic and additional agent can be the same or different. Suitable doses for the additional agents can be found in the literature.

The compounds for use in the method of the invention can be formulated for administration by any suitable route, such as for oral or parenteral, for example, transdermal, transmucosal (e.g., sublingual, lingual, (trans)buccal), vaginal (e.g., trans- and perivaginally), (intra)nasal and (trans)rectal), subcutaneous, intramuscular, intradermal, intra-arterial, intravenous, inhalation, and topical administration.

In a preferred embodiment, the compounds of the invention are formulated for intravenous delivery. In another preferred embodiment, the compounds of the invention are formulated for oral delivery. Suitable compositions and dosage forms include tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays, dry powders or aerosolized formulations.

It is preferred that the compounds are orally administered. Suitable oral dosage forms include, for example, tablets, capsules or caplets prepared by conventional means with pharmaceutically acceptable excipients such as binding agents (e.g., polyvinylpyrrolidone or hydroxypropylmethylcellulose); fillers (e.g., lactose, microcrystalline cellulose or calcium phosphate); lubricants (e.g., magnesium stearate, talc or silica); disintegrates (e.g., sodium starch glycolate); or wetting agents (e.g., sodium lauryl sulphate). If desired, the tablets can be coated, e.g., to provide for ease of swallowing or to provide a delayed release of active, using suitable methods. Liquid preparation for oral administration can be in the form of solutions, syrups or suspensions. Liquid preparations (e.g., solutions, suspensions and syrups) are also suitable for oral administration and can be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Preferably, a pharmaceutical composition comprising a ghrelin mimetic of the invention is used to treat a gastrointestinal malady (e.g., a disorder, disease, condition or injury of the gastrointestinal tract which impairs gastrointestinal kinetics) by stimulating gastrointestinal kinetics or motility. The exact formulation, route of administration and dosage can be chosen depending on the desired effect and can be made by those of skill in the art.

Dosage intervals can be determined by experimental testing. One or more ghrelin mimetics of the invention could be administered using a regimen which maintains gastrointestinal motility at about 10% above or below normal, about 20% above or below normal, above 50% above or below normal.

Another suitable administration method is to provide a ghrelin mimetic of the invention through an implant or a cell line capable of expressing a ghrelin mimetic so that the implant or cell line can provide the ghrelin mimetic to a cell of the gastrointestinal system.

A pharmaceutical composition of the invention can be formulated to be compatible with its intended route of administration.

Oral administration refers to the administration of a pharmaceutical composition of the invention via the mouth through ingestion, or via any other part of the gastrointestinal system including the esophagus or through suppository administration. Parenteral administration refers to the delivery of a composition, such as a composition comprising a ghrelin mimetic by a route other than through the gastrointestinal tract (e.g., oral delivery). In particular, parenteral administration may be via intravenous, subcutaneous, intramuscular or intramedullary (i.e., intrathecal) injection. The parenteral preparation can be enclosed in ampoules, disposable syringes or multiple dose vials made of glass or plastic. Topical administration refers to the application of a pharmaceutical agent to the external surface of the skin or the mucous membranes (including the surface membranes of the nose, lungs and mouth (in which case it may also be a form of oral administration, such that the agent crosses the external surface of the skin or mucous membrane and enters the underlying tissues. Topical administration of a pharmaceutical agent can result in a limited distribution of the agent to the skin and surrounding tissues or, when the agent is removed from the treatment area by the bloodstream, can result in systemic distribution of the agent.

In one form of topical administration contemplated by the invention, the ghrelin mimetic is delivered by transdermal delivery. Transdermal delivery refers to the diffusion of an agent across the barrier of the skin. Absorption through intact skin can be enhanced by placing the active agent in an oily vehicle before application to the skin (a process known as inunction) and the use of microneedles. Passive topical administration may consist of applying the active agent directly to the treatment site in combination with emollients or penetration enhancers. Another method of enhancing delivery through the skin is to increase the dosage of the pharmaceutical agent. The dosage for topical administration may be increased up to ten, a hundred or a thousand folds more than dosages administered by other routes.

Penetrants for transdermal delivery are generally known in the art, and include, for example, for transmucosal administration, detergents, bile salts, and fusidic acid derivatives. Transmucosal administration can be accomplished through the use of nasal sprays or suppositories. For administration by inhalation, the ghrelin mimetics of the invention can be delivered in the form of an aerosol spray from pressured container or dispenser that contains a suitable propellant, e.g., a gas such as carbon dioxide, or a nebulizer. For transdermal administration, the ghrelin mimetics of the invention can be formulated into ointments, salves, gels, or creams as generally known in the art.

In addition, the ghrelin mimetics of the invention may be delivered by nasal or pulmonary methods. The respiratory delivery of aerosolized medicaments is described in a number of references, beginning with Gansslen (1925) Klin. Wochenschr. 4:71 and including Laube et al. (1993) JAMA 269:2106-21-9; Elliott et al. (1987) Aust. Paediatr. J. 23:293-297; Wigley et al. (1971) Diabetes 20:552-556. Corthorpe et al. (1992) Pharm Res 9:764-768; Govinda (1959) Indian J. Physiol. Pharmacol. 3:161-167; Hastings et al. (1992) J. Appl. Physiol. 73:1310-1316; Liu et al. (1993) JAMA 269:2106-2109; Nagano et al. (1985) Jikeikai Med. J. 32:503-506; Sakr (1992) Int. J. Phar. 86:1-7; and Yoshida et al. (1987) Clin. Res. 35:160-166, each of which are incorporated herein by reference. Pulmonary delivery of dry powder medicaments is described in U.S. Pat. No. 5,254,330. A metered dose inhaler is described in Lee and Sciara (1976) J. Pharm. Sci. 65:567-572. The intrabronchial administration of recombinant insulin is briefly described in Schlutiter et al. (Abstract) (1984) Diabetes 33:75 A and Kohler et al. (1987) Atemw. Lungenkrkh. 13:230-232. Intranasal and respiratory delivery of a variety of polypeptides are described in U.S. Pat. No. 5,011, 678 and Nagai et al. (1984) J. Contr. Rel. 1:15-22.

Pharmaceutical compositions suitable for injectable use are known in the art and include, for example, sterile aqueous solutions (where water soluble) or dispersions and sterile powders for the extemporaneous preparation of sterile injectable solutions or dispersion. For intravenous administration of the ghrelin mimetics of the invention, physiologically acceptable, suitable carriers include, for example, physiological saline, bacteriostatic water, Cremophor EL™ (BASF, Parsippany, N.J.) or phosphate buffered saline (PBS).

Physiologically acceptable carriers maybe any carrier known in the field as suitable for pharmaceutical (i.e., topical, oral, and parenteral) application. Suitable pharmaceutical carriers and formulations are described, for example, in Remington's Pharmaceutical Sciences (19th ed.) (Genarro, ed. (1995) Mack Publishing Co., Easton, Pa.).

Oral compositions generally include a physiologically acceptable, inert diluent or an edible carrier. They can be enclosed in gelatin capsules or compressed into tablets. For the purpose of oral therapeutic administration, the ghrelin mimetics of the invention can be incorporated with physiological excipients and used in the form of tablets, troches, or capsules.

A number of systems that alter the delivery of injectable drugs can be used to change the pharmacodynamic and pharmacokinetic properties of therapeutic agents (see, e.g., K. Reddy, 2000, Annals of Pharmacotherapy 34:915-923). Drug delivery can be modified through a change in formulation (e.g., continuous-release products, liposomes) or an addition to the drug molecule (e.g., pegylation). Potential advantages of these drug delivery mechanisms include an increased or prolonged duration of pharmacologic activity, a decrease in adverse effects, and increased patient compliance and quality of life. Injectable continuous-release systems deliver drugs in a controlled, predetermined fashion and are particularly appropriate when it is important to avoid large fluctuations in plasma drug concentrations. Encapsulating a drug within a liposome can produce a prolonged half-life and an increased distribution to tissues with increased capillary permeability (e.g., tumors). Pegylation provides a method for modification of therapeutic peptides or proteins to minimize possible limitations (e.g., stability, half-life, immunogenicity) associated with the ghrelin mimetics of the invention.

In accordance with the invention, one or more ghrelin mimetics can be formulated with lipids or lipid vehicles (e.g., micelles, liposomes, microspheres, protocells, protobionts, liposomes, coacervates, and the like) to allow formation of multimers. Similarly, ghrelin mimetics can be multimerized using pegylation, cross-linking, disulfide bond formation, formation of covalent cross-links, glycosylphosphatidylinositol (GPI) anchor formation, or other established methods. The multimerized ghrelin mimetics can be formulated into a pharmaceutical composition, and used to increase or enhance their effects.

The ghrelin mimetics can also be prepared in the form of suppositories (e.g., with conventional suppository bases such as cocoa butter and other glycerides) or retention enemas for rectal delivery.

The skilled artisan will appreciate that a variety of techniques are known that can be used to deliver the ghrelin mimetics of the invention more specifically to local gastrointestinal tissues, such as, but not limited to, the stomach, esophagus, small intestine, or colon. The delivery method will depend on factors such as the tissue of interest, the nature of the compound to be delivered, and the duration of the treatment.

In one aspect, the ghrelin mimetics of the invention are prepared with carriers that will protect the ghrelin mimetics against rapid elimination from the body, such as a controlled release formulation, including implants and microencapsulated delivery systems. These can be prepared according to methods known to those skilled in the art, for example, as described in U.S. Pat. No. 4,522,811.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

EXAMPLES

The invention will now be further described by way of the following non-limiting examples.

The gastrokinetic efficacy of ipamorelin was evaluated in a rat model of post-operative ileus. In these studies ipamorelin was administered either orally (10 mg/kg and 100 mg/kg) or via a single intravenous injection was administered to male rats following abdominal surgery over a dose range of 0.01 mg/kg to 1.0 mg/kg. The effect of ipamorelin on gastric emptying relative to control animals was determined by administration of a dose of phenol red via oral gavage followed immediately with the dose of ipamorelin.

Example 1

Gastrokinetic Efficacy of Ipamorelin (10 or 100 mg/kg) in a Rat Model of Post-Operative Ileus This study evaluated the potential gastrokinetic efficacy of ipamorelin following a single oral administration in a rat model of post-operative ileus at a dose of 10 or 100 mg/kg.

| Treatment Group | Dose level (mg/kg) | Dose concentration (mg/mL) | Dose volume (mL/kg) | No. of males |
|---|---|---|---|---|
| 1 Vehicle/control | 0 | 0 | 5 | 8 |
| 2 Ipamorelin | 10 | 2 | 5 | 8 |
| 3 Ipamorelin | 100 | 20 | 5 | 8 |

* Animals in this group underwent all surgical procedures but with no cecum manipulation.

Methods and Experimental Design

Male Sprague-Dawley CD® (Crl: CD® (SD)) rats (*Rattus norvegicus*) were received from Charles River Canada Inc. St. Constant, Quebec, Canada.

Nine days were allowed between receipt of the animals and the start of treatment to accustom the animals to the laboratory environment. At the start of treatment, animals were approximately 7 weeks of age and were in the weight range of 230 g to 254 g.

Animals were housed individually in stainless steel wire mesh-bottomed cages equipped with an automatic watering valve. Each cage was clearly labeled with a color-coded cage card indicating project, group, animal numbers and sex. Each animal was uniquely identified. The targeted conditions for animal room environment and photoperiod were as follows: Temperature 22±3° C.; Humidity 50±20%; Light Cycle 12 hours light and 12 hours dark.

All animals were given free access (except during designated procedures) to a standard certified pelleted commercial laboratory diet (PMI Certified Rodent Chow 5002: PMI Nutrition International Inc.). The diet was controlled and routinely analyzed by the manufacturer for maximum allowable concentrations of contaminants (eg, heavy metals, aflatoxins, organophosphates, chlorinated hydrocarbons and PCBs). Municipal tap water which had been softened, purified by reverse osmosis and exposed to ultraviolet light was provided ad libitum (except during designated procedures). It is considered that there were no known contaminants in the dietary materials that could have influenced the outcome of the study.

The ipamorelin obtained and used in this study was obtained from Bachem A G (Bubendorf, Switzerland). The vehicle used was 0.9% sodium chloride for injection (Baxter). The gastrointestinal marker used to evaluate level stomach emptying was phenol red (Sigma Aldrich).

Appropriate amounts of test article were dissolved in 0.9% Sodium Chloride for Injection USP. The test article formulations were adjusted between pH 7.4 to with 0.1N/1N hydrochloric acid or 0.1N sodium hydroxide, as required. All dosing formulations were kept at room temperature, protected from light. The phenol red was prepared on the day of dosing as a 5 mg/mL solution in deionized water and was stored at room temperature, protected from light.

Catheterization Surgery

Each animal received an antibiotic injection of Benzathine penicillin G and Procaine penicillin G (0.1 mL) intramuscularly on the day of surgery and again 2 days following surgery. The animals were anesthetized with isoflurane gas prior to surgery preparation, which included shaving of the femoral and dorsal exteriorization sites. The shaved areas were washed with Chlorhexidine gluconate 4% followed by a liberal application of Povidone iodine 10%. Prior to surgery and at the end of the surgical procedure, while under anesthesia, a bland lubricating ophthalmic agent (Tears Naturale PM) was administered to each eye. Animals were maintained under isoflurane gas anesthesia throughout the surgical procedure.

A small incision was made in the right groin region and the femoral vein was isolated. A small phlebotomy was made in the vein and a medical grade silicone-based catheter was inserted and the tip of the catheter was placed in the vena cava at approximately the level of the kidneys. The catheter was secured in place with an appropriate suture material and then brought subcutaneously to the exteriorization point at the nape of the neck. The femoral site was irrigated with warm (approximately 37° C.) 0.9% Sodium Chloride Injection, USP. The femoral site was closed with interrupted mattress sutures and the exteriorization site with a purse stitch, which was removed in 5-10 days or depending upon healing results. A topical antibiotic (Polymyxin B, Bacitracin, Neomycin) was administered to the catheter exteriorization site, daily until termination, and the femoral site until considered unnecessary.

A jacket was placed on the animal to hold the tether system. The catheter, prefilled with 0.9% Sodium Chloride Injection, U.S.P., was fed through the tether system and attached to a swivel secured to the outside of the cage. The upper portion of the swivel was connected to the infusion pump and all animals were continuously infused with 0.9% Sodium Chloride Injection, U.S.P. at a rate of 0.4 mL/h until initiation of treatment.
Surgery to Induce Post-Operative Ileus All treatment procedures were replicated over two consecutive days with approximately equal numbers of animals from each group treated on each day. Food was withdrawn from animals overnight prior to surgery. On the day of surgery animals were anesthetized with isoflurane gas and a bland ophthalmic lubricant (Tears Naturale PM) was applied to each eye. The animals were prepared for surgery by shaving of the entire abdominal region. The shaved area was cleaned and disinfected appropriately prior to incision. Using a scalpel blade, the abdomen was opened and the cecum localized. The cecum was exteriorized and manipulated for approximately one minute (i.e. gently patted between hands in saline-soaked gauze). Thereafter, the cecum was repositioned and the surgical site closed using absorbable suture material (interrupted sutures) and staples. Animals were then returned to their home cage to permit recovery from the anesthesia.

Animals assigned to the sham control group (Group 1) underwent the same treatment procedures, with the exception that the cecum was exteriorized and repositioned without manipulation.
Dose Administration Dosing commenced on consecutive days with approximately equal numbers of animals from each group being dosed on each day. Prior to dosing, the animals were water deprived. The test/control articles were administered by oral gavage using a syringe and flexible gavage tube. The animals were dosed immediately following the oral gavage dose of phenol red. The dose volume was 5 mL/kg (for both ipamorelin and phenol red administration) and the actual dose administered was based on the most recent body weight of each animal.
Gastrointestinal Assessment Approximately 30 minutes following the morphine injection, all animals received 0.4 mL of phenol red by oral gavage. Approximately 30 minutes following administration of control or test article, the rats were euthanized. The stomach was then exposed by laparotomy, quickly ligated at the pylorus and the cardia and removed. The stomach was cut open and its contents extracted with 100 mL of 0.1N NaOH. The phenol red content of this extract was assayed calorimetrically at 558 nm in a spectrophotometer. Following collection, samples were stored on wet ice pending transfer for analysis.
Results Orally administered following post-operative ileus, ipamorelin accelerated stomach emptying by approximately 12.4% and 41.6% at 10 and 100 mg/kg, respectively, when compared to the control animals, without, however, attaining statistical significance. See FIG. 1.
Conclusion Ipamorelin administered orally at doses of 10 or 100 mg/kg accelerated emptying in a dose dependent relationship, in a rat model of post-operative ileus.

Example 2

Gastrokinetic Efficacy of Intravenous-Administered Ipamorelin (0.1, 0.25 or 1.0 mg/kg) in a Rat Model of Post-Operative Ileus In this study ipamorelin was administered as a slow bolus intravenous injection via an indwelling catheter (over a period of ca. 100 seconds).

| Treatment Group | Dose level (mg/kg) | Dose concentration (mg/mL) | Dose volume (mL/kg) | No. of males |
|---|---|---|---|---|
| 1 Sham*/Vehicle | 0 | 0 | 5 | 8 |
| 2 Surgery/Vehicle | 0 | 0 | 5 | 8 |
| 3 Surgery/ipamorelin | 0.1 | 0.02 | 5 | 8 |
| 4 Surgery/ipamorelin | 0.25 | 0.05 | 5 | 8 |
| 5 Sugery/ipamorelin | 1.0 | 0.2 | 5 | 8 |

*Animals in this group underwent all surgical procedures but with no cecum manipulation.

Methods and Experimental Design

Male Sprague-Dawley CD® (Crl: CD®(SD)) rats (*Rattus norvegicus*) were received from Charles River Canada Inc. St. Constant, Quebec, Canada. Eight days were allowed between receipt of the animals and the surgical implantation of the catheters to allow the animals to become acclimated to the physical and environmental conditions. Dosing of the animals was initiated approximately one week following surgical implantation of the catheters to allow appropriate recovery of the animals prior to treatment. At the start of treatment, animals were approximately between 10 to 12 weeks of age and were in the weight range of 327 g to 397 g.

Animals were housed individually in stainless steel wire mesh-bottomed cages equipped with an automatic watering valve. Each cage was clearly labeled with a color-coded cage card indicating project, group, animal numbers and sex. Each animal was uniquely identified. The targeted conditions for animal room environment and photoperiod were as follows: Temperature 22±3° C.; Humidity 50±20%; Light Cycle 12 hours light and 12 hours dark.

All animals were given free access (except during designated procedures) to a standard certified pelleted commercial laboratory diet (PMI Certified Rodent Chow 5002: PMI Nutrition International Inc.). The diet was controlled and routinely analyzed by the manufacturer for maximum allowable concentrations of contaminants (eg, heavy metals, aflatoxins, organophosphates, chlorinated hydrocarbons and PCBs). Municipal tap water which had been softened, purified by reverse osmosis and exposed to ultraviolet light was provided ad libitum (except during designated procedures). It is considered that there were no known contaminants in the dietary materials that could have influenced the outcome of the study.

The ipamorelin obtained and used in this study was obtained from Bachem A G. The vehicle used was 0.9% sodium chloride for injection (Baxter). The gastrointestinal marker used to evaluate level stomach emptying was phenol red (Sigma Aldrich).

Catheterization Surgery

Each animal received an antibiotic injection of Benzathine penicillin G and Procaine penicillin G (0.1 mL) intramuscularly on the day of surgery and again 2 days following surgery. The animals were anesthetized with isoflurane gas prior to surgery preparation, which included shaving of the femoral and dorsal exteriorization sites. The shaved areas were washed with Chlorhexidine gluconate 4% followed by a liberal application of Povidone iodine 10%. Prior to surgery and at the end of the surgical procedure, while under anesthesia, a bland lubricating ophthalmic agent (Tears Naturale PM) was administered to each eye. Animals were maintained under isoflurane gas anesthesia throughout the surgical procedure.

A small incision was made in the right groin region and the femoral vein was isolated. A small phlebotomy was made in the vein and a medical grade silicone-based catheter was inserted and the tip of the catheter was placed in the vena cava at approximately the level of the kidneys. The catheter was secured in place with an appropriate suture material and then brought subcutaneously to the exteriorization point at the nape of the neck. The femoral site was irrigated with warm (approximately 37° C.) 0.9% Sodium Chloride Injection, USP. The femoral site was closed with interrupted mattress sutures and the exteriorization site with a purse stitch, which was removed in 5-10 days or depending upon healing results. A topical antibiotic (Polymyxin B, Bacitracin, Neomycin) was administered to the catheter exteriorization site, daily until termination, and the femoral site until considered unnecessary.

A jacket was placed on the animal to hold the tether system. The catheter, prefilled with 0.9% Sodium Chloride Injection, U.S.P., was fed through the tether system and attached to a swivel secured to the outside of the cage. The upper portion of the swivel was connected to the infusion pump and all animals were continuously infused with 0.9% Sodium Chloride Injection, U.S.P. at a rate of 0.4 mL/h until initiation of treatment.

Surgery to Induce Post-Operative Ileus

All treatment procedures were replicated over two consecutive days with approximately equal numbers of animals from each group treated on each day. Food was withdrawn from animals overnight prior to surgery. On the day of surgery animals were anesthetized with isoflurane gas and a bland ophthalmic lubricant (Tears Naturale PM) was applied to each eye. The animals were prepared for surgery by shaving of the entire abdominal region. The shaved area was cleaned and disinfected appropriately prior to incision. Using a scalpel blade, the abdomen was opened and the cecum localized. The cecum was exteriorized and manipulated for approximately one minute (i.e. gently patted between hands in saline-soaked gauze). Thereafter, the cecum was repositioned and the surgical site closed using absorbable suture material (interrupted sutures) and staples. Animals were then returned to their home cage to permit recovery from the anesthesia.

Animals assigned to the sham control group (Group 1) underwent the same treatment procedures, with the exception that the cecum was exteriorized and repositioned without manipulation. Note that due to technical oversight, the cecums of animal Nos. 2001, 2009, 3001 and 4001 were manipulated with sterile water for injection USP instead of saline soaker gauze. This minor deviation was considered to have had no impact on the study outcome or upon the interpretation of the results.

Dose Administration

Dosing commenced on consecutive days with approximately equal numbers of animals from each group being dosed on each day. The test/control articles were administered as a slow bolus intravenous injection via an indwelling catheter (over a period of ca. 100 seconds). The animals were dosed immediately following the oral gavage dose of phenol red. The dose volume was 5 mL/kg (for both ipamorelin and phenol red administration) and the actual dose administered was based on the most recent body weight of each animal.

Gastrointestinal Assessment

Prior to dosing of the phenol red, the animals were water deprived. At approximately 30 minutes post-surgery (ileus), animals received 0.4 mL of phenol red by oral gavage. Animals were then dosed and approximately 30 minutes later, were euthanized. Upon euthanasia, the stomach was exposed by laparotomy, quickly ligated at the pylorus and the cardia removed. The stomach was cut open and its contents extracted with 100 mL of 0.1N NaOH. The phenol red content of this extract was assayed calorimetrically at 558 nm in a spectrophotometer. Following collection, samples were stored on wet ice pending transfer for analysis.

Results

Figure 2:
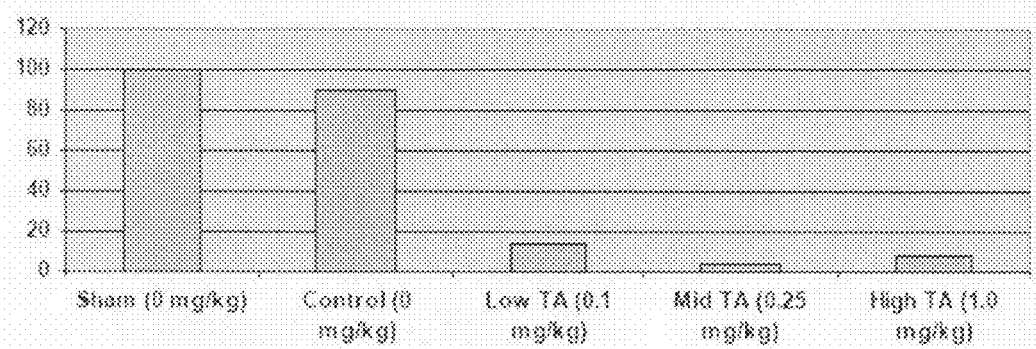
FIG. 2 shows the efficacy of i.v. administered ipamorelin at 0.1, 0.25 or 1.0 mg/kg on a rat model of post-operative ileus.

Intravenously administered ipamorelin at doses of 0.1, 0.25 and 1.0 mg/kg following surgery accelerated stomach emptying in the male albino rats when compared to the vehicle control and sham control animals, although a dose relationship was not observed. Animals treated with an intravenous dose (0.1, 0.25 or 1.0 mg/kg) of ipamorelin displayed a reduction in stomach phenol red content relative to the vehicle control group (85.7%, 95.6% and 92.2%, respectively). These reductions reached statistical significance at the 0.25 and 1.0 mg/kg dose levels ($p \leq 0.001$ and $p \leq 0.01$, respectively). See FIG. 2.

The average stomach phenol red content of the vehicle control group was similar and not statistically different from that of the sham control group and may reflect (unexpected) ileus in the sham control group or an inability to induce detectable ileus in the surgery control group. Consequently, when expressed relative to the sham control group, animals treated with intravenous doses (0.1, 0.25 or 1.0 mg/kg) of ipamorelin displayed reductions in stomach phenol red content (87.1%, 96.0% and 93.1%, respectively) that were statistically significant at all dose levels. See FIG. 2.

Conclusion

Ipamorelin administered intravenously to male albino rats at a dose of 0.1, 0.25 and 1.0 mg/kg following surgery significantly accelerated stomach emptying when compared to the sham and vehicle control animals.

Example 3

Gastrokinetic Efficacy of Intravenous-Administered Ipamorelin (0.01, 0.03 or 0.1 mg/kg) in a Rat Model of Post-Operative Ileus In this study ipamorelin was administered as a slow bolus intravenous injection via an indwelling catheter (over a period of ca. 100 seconds) at a dose of 0.01, 0.03 or 0.1 mg/kg.

| Treatment Group | Dose level (mg/kg) | Dose concentration (mg/mL) | Dose volume (mL/kg) | No. of males |
|---|---|---|---|---|
| 1 Non-operated control* | 0 | 0 | 5 | 8 |
| 2 Surgery/ Vehicle | 0 | 0 | 5 | 8 |
| 3 Surgery/ ipamorelin | 0.01 | 0.02 | 0.5 | 8 |
| 4 Surgery/ ipamorelin | 0.03 | 0.02 | 1.5 | 8 |
| 5 Sugery/ ipamorelin | 0.1 | 0.02 | 5 | 8 |

*Animals in this group did not undergo surgery for ileus induction.

Male Sprague-Dawley CDs (Crl: CD® (SD)) rats (*Rattus norvegicus*) were used. Seven days were allowed between receipt of the animals and the surgical implantation of the catheters to allow the animals to become acclimated to the physical and environmental conditions. Dosing of the animals was initiated approximately one week following surgical implantation of the catheters to allow appropriate recovery of the animals prior to treatment. At the start of treatment, animals were approximately 10 weeks of age and were in the weight range of 334 g to 385 g.

Animals were housed individually in stainless steel wire mesh-bottomed cages equipped with an automatic watering valve. The targeted conditions for animal room environment and photoperiod were as follows: Temperature: 22±3° C.; Humidity: 50±20%; Light cycle: 12 hours light and 12 hours dark. All animals were examined twice daily for mortality and signs of ill health or reaction to treatment (except on the day of arrival and necropsy when the animals were examined once). Individual body weights were measured at randomization and on the day prior to dosing (for dose calculation purposes only).

Catheterization Surgery

A small incision was made in the right groin region and the femoral vein was isolated. A small phlebotomy was made in the vein and a medical grade silicone-based catheter was inserted and the tip of the catheter was placed in the vena cava at approximately the level of the kidneys. The catheter was secured in place with an appropriate suture material and then brought subcutaneously to the exteriorization point at the nape of the neck. The femoral site was irrigated with warm (approximately 37° C.) 0.9% Sodium Chloride Injection, USP. The femoral site was closed with interrupted mattress sutures and the exteriorization site with a purse stitch, which was removed in 5-10 days or depending upon healing results. A topical antibiotic (Polymyxin B, Bacitracin, Neomycin) was administered to the catheter exteriorization site, daily until termination, and the femoral site until considered unnecessary.

A jacket was placed on the animal to hold the tether system. The catheter, prefilled with 0.9% Sodium Chloride Injection, U.S.P., was fed through the tether system and attached to a swivel secured to the outside of the cage. The upper portion of the swivel was connected to the infusion pump and all animals were continuously infused with 0.9% Sodium Chloride Injection, U.S.P. at a rate of 0.4 mL/h until initiation of treatment.

Surgery to Induce Post-Operative Ileus

All treatment procedures were replicated over two consecutive days with approximately equal numbers of animals from each group treated on each day. Food was withdrawn from animals overnight prior to surgery. On the day of surgery animals were anesthetized with isoflurane gas and a bland ophthalmic lubricant (Tears Naturale PM) was applied to each eye. The animals were prepared for surgery by shaving of the entire abdominal region. The shaved area was cleaned and disinfected appropriately prior to incision. Using a scalpel blade, the abdomen was opened and the cecum localized. The cecum was exteriorized and manipulated for approximately one minute (i.e. gently patted between hands in saline-soaked gauze). Thereafter, the cecum was repositioned and the surgical site closed using absorbable suture material (interrupted sutures) and staples. Animals were then returned to their home cage to permit recovery from the anesthesia.

Animals assigned to the non-operated control group (Group 1) did not undergo surgery to induce post-operative ileus.

Dose Administration

Dosing commenced on consecutive days with approximately equal numbers of animals from each group being dosed on each day. The test/control articles were administered as a slow bolus intravenous injection via an indwelling catheter. The animals were dosed immediately following the oral gavage dose of phenol red. The dose volume was 5 mL/kg for Groups 1, 2 and 5; 0.5 mL/kg for Group 3 and 1.5 mL/kg for Group 4. The actual dose administered was based on the most recent body weight of each animal.

Gastrointestinal Assessment

Prior to dosing of the phenol red, the animals were water deprived. At approximately 30 minutes post-surgery (ileus), animals received 0.4 mL of phenol red by oral gavage. Animals were then dosed and approximately 30 minutes later, were euthanized. Upon euthanasia, the stomach was exposed by laparotomy, quickly ligated at the pylorus and the cardia removed. The stomach was cut open and its contents extracted with 100 mL of 0.1 N NaOH. The phenol red content of this extract was assayed calorimetrically at 558 nm in a spectrophotometer. Following collection, samples were stored on wet ice pending transfer for analysis.

Results

Figure 3:
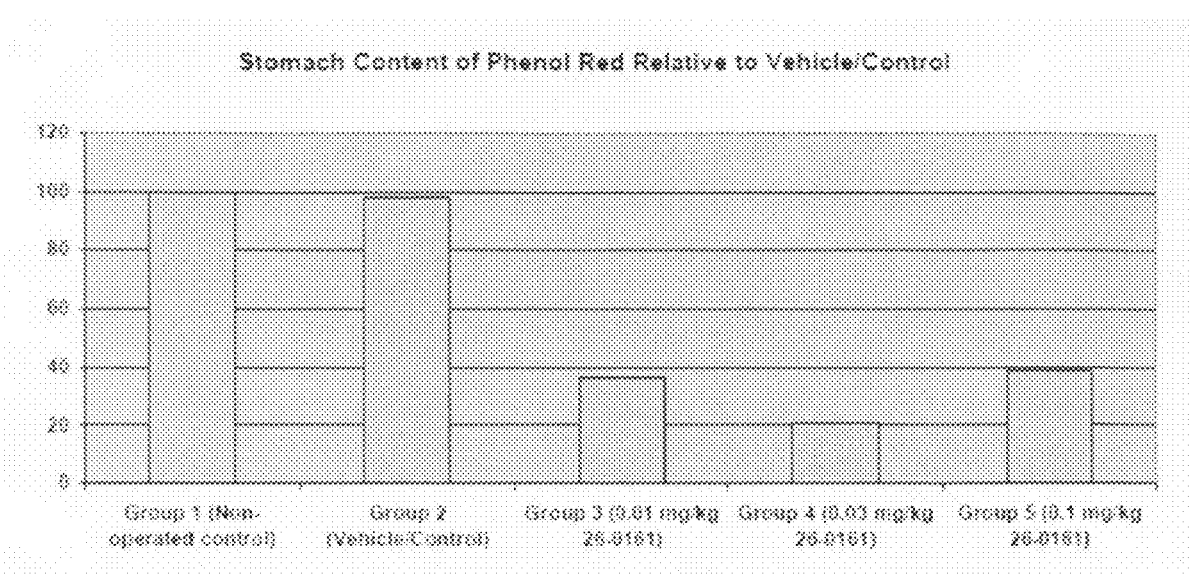
FIG. 3 shows the efficacy of i.v. administered ipamorelin at 0.01, 0.03 and 0.1 mg/kg in a rat model for post-operative ileus.

Intravenously administered ipamorelin at doses of 0.01, 0.03 and 0.1 mg/kg following surgery accelerated stomach emptying in the male albino rats when compared to the vehicle control and non-operated control animals, although a dose relationship was not observed. Animals treated with intravenous doses (0.01, 0.03 or 0.1 mg/kg) of ipamorelin displayed reductions in stomach phenol red content relative to the vehicle control group. These reductions reached statistical significance at all dose levels ($p \leq 0.05$ at 0.01 and 0.1 mg/kg and $p \leq 0.0$ at 0.03 mg/kg). See FIG. 3.

The average stomach phenol red content of the vehicle control group was similar and not statistically different from that of the non-operated control group and may reflect an inability to induce detectable ileus in the surgery control group. Consequently, when expressed relative to the non-operated control group, animals treated with intravenous doses (0.01, 0.03 or 0.1 mg/kg) of ipamorelin displayed reductions in stomach phenol red content that were statistically significant at all dose levels.

Example 4

Efficacy of Morphine to Induce Gastric Ileus in Rats

The purpose of this study was to evaluate the potential efficacy of morphine to induce gastric ileus in rats. Treatment groups were set up as follows.

| Treatment Group | Morphine Dose level (mg/kg) | Ghrelin Dose level (ug/kg) | Ghrelin concentration (ug/mL) | Dose volume (mL/kg) | No. of males |
|---|---|---|---|---|---|
| 1 Saline control | 0 | 0 | 0 | 1.5 | 8 |
| 2 Morphine + saline | 1* | 0 | 0 | 1.5 | 8 |
| 3 Morphine + ghrelin | 1* | 50 | 33.33 | 1.5 | 8 |
| 4 Morphine + saline | 4** | 0 | 0 | 1.5 | 8 |
| 5 Morphine + ghrelin | 4** | 50 | 33.33 | 1.5 | 8 |

*Morphine was administered at a dose volume of 0.1 mL/kg for groups 2-3
**Morphine was administered at a dose volume of 0.4 mL/kg for groups 4-5

Methods and Experimental Design

Male Sprague-Dawley CD® (Crl: CD®(SD)) rats (*Rattus norvegicus*) were received from Charles River Canada Inc. St. Constant, Quebec, Canada. Subsequent to arrival, all animals were subjected to a general physical examination by a qualified member of the veterinary staff to ensure normal health status. All animals were considered acceptable for use. Nine days were allowed between receipt of the animals and the start of treatment to accustom the animals to the laboratory environment. At the start of treatment, animals were approximately between 7 weeks of age and were in the weight range of 231 g to 267 g. Please note that the animals body weights were slightly outside the protocol stated range. This deviation was considered to have had no impact on the outcome of the study or upon interpretation of the results.

Animals were housed individually in stainless steel wire mesh-bottomed cages equipped with an automatic watering valve. The targeted conditions for animal room environment and photoperiod were as follows: Temperature 22±3° C.; Humidity 50±20%; Light Cycle 12 hours light and 12 hours dark.

All animals were given free access (except during designated procedures) to a standard certified pelleted commercial laboratory diet (PMI Certified Rodent Chow 5002: PMI Nutrition International Inc.). The diet was controlled and routinely analyzed by the manufacturer for maximum allowable concentrations of contaminants (eg, heavy metals, aflatoxins, organophosphates, chlorinated hydrocarbons and PCBs). The results of these analyses are retained in the scientific archives of PCS-MTL. Municipal tap water which had been softened, purified by reverse osmosis and exposed to ultraviolet light was provided ad libitum (except during designated procedures). Periodic analysis of the water was subcontracted to management authorized analytical laboratories which were audited by the Quality Assurance department of PCS-MTL. The results of these analyses are retained in the scientific archives of PCS-MTL. It is considered that there were no known contaminants in the dietary materials that could have influenced the outcome of the study.

The dose formulations were prepared on the day of dosing. The appropriate control was dissolved in the vehicle to achieve the desired concentration. The morphine sulfate solution was used as supplied. The phenol red was prepared on the day of dosing as a 5 mg/mL solution and stored at room temperature, protected from light pending use.

Dose Administration

Morphine (4 mg/kg or 1 mg/kg) was administered once to the upper dorsum (scapular region) by subcutaneous injection using a hypodermic needle attached to a syringe. Morphine was administered approximately 30 minutes prior to the administration of the control/positive control articles. The dose volume was 0.1 mL/kg for Groups 2 and 3 and 0.4 mL/kg for Groups 4 and 5. The actual dose administered was based on the most recent practical body weight of each animal.

Gastrointestinal Assessment

Approximately 30 minutes following the morphine injection, all animals received 0.4 mL of phenol red by oral gavage. Approximately 30 minutes following administration of control or test article, the rats were euthanized. The stomach was then exposed by laparotomy, quickly ligated at the pylorus and the cardia and removed. The stomach was cut open and its contents extracted with 100 mL of 0.1N NaOH. The phenol red content of this extract was assayed calorimetrically at 558 nm in a spectrophotometer. Following collection, samples were stored on wet ice pending transfer for analysis.

Results

Figure 4:
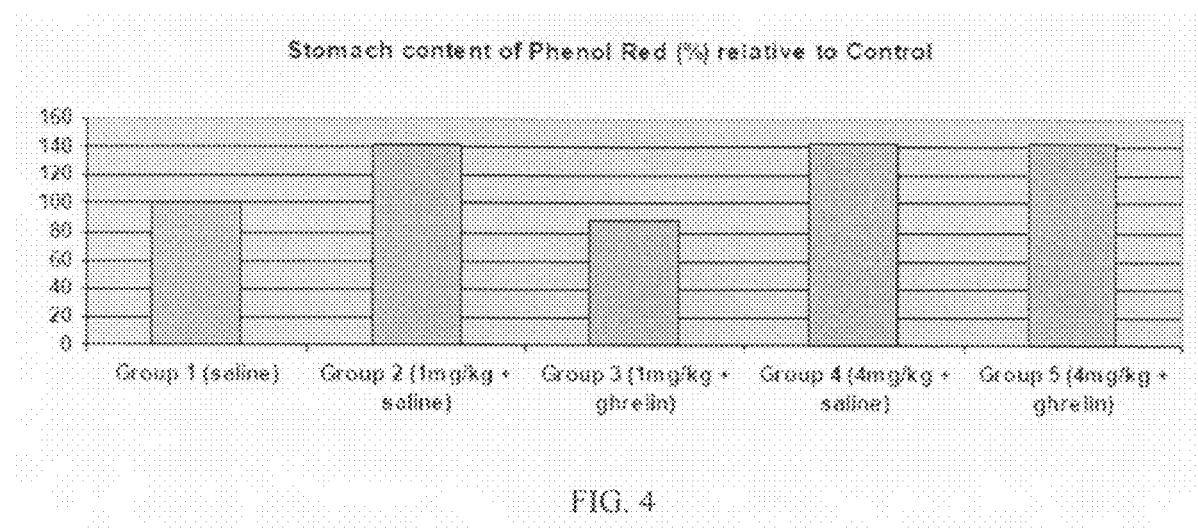
FIG. 4 demonstrates that ghrelin did not accelerate gastric emptying in the rats administered 4 mg/kg of morphine and that rats administered saline or ghrelin displayed the same group mean absorbance of phenol red.

Subcutaneously administered at a dose of 1 or 4 mg/kg, morphine significantly reduced the stomach emptying by approximately 42% when compared to the control animals, without however attaining statistical significance. Ghrelin, a potent prokinetic peptide known to reverse gastric ileus, administered intravenously at a dose of 50 µg/kg following exposure with 1 mg/kg of morphine, accelerated stomach emptying by approximately 37% when compared to the animals treated with 1 mg/kg and saline, and reversed the ileus induced by approximately 11%. However, ghrelin did not accelerate gastric emptying in the rats administered 4 mg/kg of morphine and both groups (saline vs ghrelin) displayed the same group mean absorbance of phenol red (2.99 and 3.01, respectively). See FIG. 4.

Conclusion

Morphine administered subcutaneously to male albino rats at doses of 1 or 4 mg/kg induced similar level of gastric ileus, in a non dose-dependent manner. Ghrelin accelerated stomach emptying and reversed the gastric ileus induced following exposure with 1 mg/kg of morphine but had no effects on the stomach emptying of the rats administered doses of 4 mg/kg of morphine.

Example 5

Gastrokinetic Efficacy of Intravenous Injection of Ipamorelin (1.0, 2.5, 10 mg/kg) as Compared to RC-1139 to Treat Post-Operative Ileus in a Rat Model Ipamorelin was evaluated in a rat model of post-operative ileus in comparison to RC-1139, a ghrelin mimetic with known gastrokinetic efficacy. In this study each drug was administered as a single intravenous injection as shown in the table below. Treatment groups were as follows.

| Treatment Group | Dose level (mg/kg) | Dose concentration (mg/mL) | Dose volume (mL/kg) | No. of males |
|---|---|---|---|---|
| 1 Vehicle/Control | 0 | 0 | 5 | 8 |
| 2 Ipamorelin | 1 | 0.2 | 5 | 8 |
| 3 Ipamorelin | 2.5 | 0.5 | 5 | 8 |
| 4 Ipamorelin | 10/0.25 | 2.5/0.05 | 5 | 8* |
| 5 RC-1139 (reference article) | 10 | 2 | 5 | 8 |

*Lethality was observed immediately following administration of a 10 mg/kg dose (n = 2) and consequently the dose level was reduced to 0.25 mg/kg for all remaining animals in Group 4

All animals were examined twice daily for mortality and signs of ill health or reaction to treatment (except on the day of arrival and necropsy when the animals were examined once). Individual body weights were measured at randomization and on the day prior to dosing (for dose calculation purposes only). Two animals died immediately following administration of ipamorelin at a dose of 10 mg/kg and consequently all remaining animals from Group 4 were dosed at 0.25 mg/kg.

Methods and Experimental Design

Male Sprague-Dawley CD® (Crl: CD® (SD)) rats (*Rattus norvegicus*) were randomized to treatment groups At least 5 days was allowed between receipt of the animals and the start of treatment to accustom the animals to the laboratory environment. At the start of treatment, animals were approximately 7 weeks of age and were in the weight range of 205 g to 272 g.

Prior to the first dose formulation preparation, a trial preparation was conducted at 2 mg/mL (test article solution) and at 2 mg/mL (reference article solution) to confirm the suitability of the proposed formulation method.

For dosing, formulations were prepared by dissolving the appropriate quantity of test or reference article in 0.9% Sodium Chloride for Injection USP. The dosing formulations were then pH adjusted from 7.4 to 7.5 with 0.1N/1N hydrochloric acid or 0.1N sodium hydroxide, as required. All dosing formulations were filtered via 0.2 µm PVDF filters prior to use and were kept at room temperature, protected from light.

The phenol red was prepared on the day of dosing as a 5 mg/mL solution in deionized water and was stored at room temperature, protected from light.

Surgery to Induce Post-Operative Ileus

All treatment procedures were replicated over two consecutive days with approximately equal numbers of animals from each group treated on each day. Food was withdrawn from animals overnight prior to surgery. On the day of surgery animals were anesthetized with isoflurane gas and a bland ophthalmic lubricant was applied to each eye. The animals were prepared for surgery by shaving of the entire abdominal region. The shaved area was cleaned and disinfected appropriately prior to incision. Using a scalpel blade, the abdomen was opened and the cecum localized. The cecum was exteriorized and manipulated for approximately one minute (i.e. gently patted between hands in saline-soaked gauze). Thereafter, the cecum was repositioned and the surgical site closed using absorbable suture material (interrupted sutures) and staples. Animals were then returned to their home cage to permit recovery from the anesthesia.

Dose Administration

Animals were dosed immediately following the oral gavage dose of phenol red. The test/control articles and reference article were administered by intravenous injection (given as a slow bolus injection over a period of ca. 100 seconds) into the tail vein using a syringe and appropriate gauge needle. The dose volume was 5 mL/kg and the actual dose administered was based on the most recent body weight of each animal.

Gastrointestinal Assessment

Prior to dosing of the phenol red, the animals were water deprived. At approximately 30 minutes post-surgery, animals received 0.4 mL of phenol red by oral gavage, then dosed with the test article, and then, approximately 30 minutes later, were euthanized. Upon euthanasia, the stomach was exposed by laparotomy, quickly ligated at the pylorus and the cardia and removed. The stomach was cut open and its contents extracted with 100 mL of 0.1N NaOH. The phenol red content of this extract was assayed calorimetrically at 558 nm in a spectrophotometer. Following collection, samples were stored on wet ice pending transfer for analysis.

Results

Figure 5:
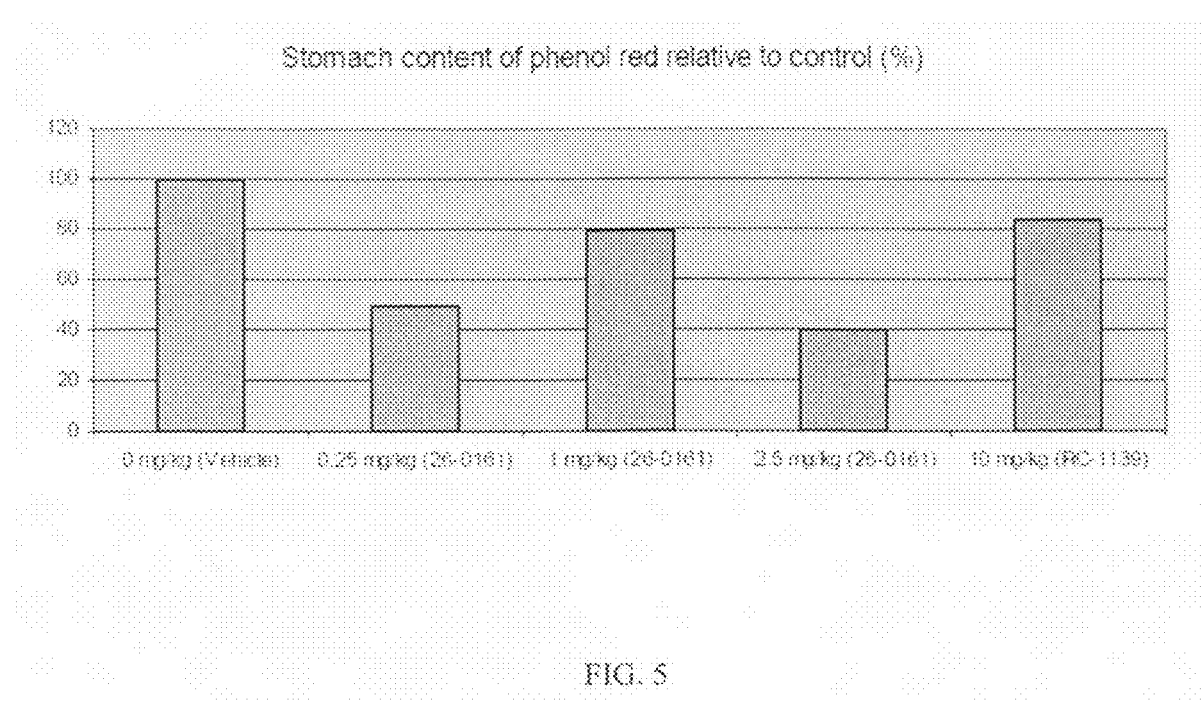
FIG. 5 shows the gastrokinetic efficacy of intravenous administration of ipamorelin (referred to as 26-0161 in the figure) at 0.25, 1.0, 2.5 mg/kg as compared to 10 mg/kg RC-1139 to treat post-operative ileus in a rat model.

Ipamorelin administered intravenously at doses of 0.25, 1 and 2.5 mg/kg following induction of a post-operative ileus accelerated stomach emptying in the male albino rats, when compared to the control and RC-1139 treated animals, although a monotonic dose relationship was not observed. See FIG. 5.

Intravenous doses of 0.25 and 2.5 mg/kg each displayed a similar level of efficacy with approximately 50 and 60% reductions in phenol red content, respectively, while approximately 21% emptying was observed following the 1 mg/kg dose. The stomach content of the phenol red marker following administration of the 10 mg/kg RC-1139 dose was approximately 16% lower than that of the control group.

Conclusion

Ipamorelin administered intravenously at doses of 0.25, 1 and 2.5 mg/kg to male albino rats with post-operative ileus accelerated stomach emptying, when compared to the control and reference animals.

Example 6

Administration of Ipamorelin in Healthy Volunteers to Reverse a Morphine-Induced Slowing of Gastric Emptying Introduction Delay in gastric emptying plays an etiologic role in several important target indications including post-operative ileus, opiate-induced bowel dysfunction, and gastroparesis. In addition, delays in gastric emptying may promote or exacerbate nausea. Consequently, an agent such as ipamorelin, with demonstrated ability to promote gastric emptying in animal models (see above Examples), may serve an important therapeutic role in a variety of GI disorders categorized by reduced motility.

Ipamorelin is a ghrelin mimetic. Ghrelin, a 28-amino acid peptide hormone, is primarily synthesized in the oxyntic gland in the stomach and to a lesser degree in other organs of the body such as the kidney and hypothalamus. Among the important physiologic effects exerted by ghrelin is its ability to modulate gastric motility and it has demonstrated a strong prokinetic effect (both upper and lower GI) in a variety of animal species as well as humans. See Masuda 2000, Asakawa 2001, Tack 2006. Additionally, in a rat model ghrelin has been shown to resolve gastric postoperative ileus. See Trudel 2002.

The prokinetic activity of ghrelin is likely mediated either by direct effect on the gut or indirectly by the vagal-cholinergic-muscarinic pathway. It acts locally in the stomach to stimulate the firing of vagal afferent neurons and stimulate gastric motility. See Peeters 2003. Efforts have been underway for many years to exploit the positive effects of ghrelin in a variety of disorders via the identification and development of pharmaceutical agents that mimic ghrelin. Ghrelin has an exceptionally short half-life (approximately 10 minutes) in humans and consequently has a limited therapeutic potential. Ipamorelin is a ghrelin mimetic with a half-life of approximately six hours in humans, available as an intravenous treatment and thus, is suitable for therapeutic use.

The present study was designed to employ a well-validated, clinical pharmacology model (acetaminophen AUC) for assessment of the effect of ipamorelin on gastric emptying. Ipamorelin was demonstrated in the examples described above to have potent, stimulating effects on gastric emptying in a rat model. This study was intended to extend these findings into humans.

Dosages

The dose of ipamorelin selected for this study (0.06 mg/kg IV infused over 15 minutes), was a dose that has been demonstrated to be safe and well-tolerated in prior Phase 1 studies. Ipamorelin was formulated as a 0.5 mg/mL sterile solution with 2 equivalents of acetic acid in normal saline. The sterile solution was further diluted with normal saline to an appropriate volume for administration prior to use.

The dose of morphine selected for this study (0.05 mg/kg IV bolus) was a dose that is both clinically relevant as an analgesic dose and has been demonstrated previously to significantly delay gastric emptying in normal volunteers [Yuan 1998].

The acetaminophen dose selected for this study (1000 mg oral suspension) is a standard Over-the-Counter dose of acetaminophen. This dose has been employed successfully in prior gastric emptying studies and produces plasma concentrations which are readily measured (>0.2 µg/mL).

The study design was a standard, three-period, randomized, single-dose crossover study.

This study was carried out with single-dose administrations, which is appropriate and well-studied in the acetaminophen AUC model of gastric emptying. All of the three drugs employed in the present study have terminal half-lives of six hours or less, consequently a washout interval of 5-8 days will ensure complete elimination of the drugs from the body.

This study's objectives included assessing the ability of intravenous ipamorelin to reverse opiate-induced delay in gastric emptying as well as assessing the ability of intravenous ipamorelin to reverse opiate-induced nausea. The inventors predicted that ipamorelin will reverse opiate-induced delay in gastric emptying as assessed by plasma acetaminophen absorption: the plasma acetaminophen $AUC_{0-60}$ following ipamorelin administration will be 50% greater than that following placebo.

Study Design

The study was conducted as a single-center, double-blind, randomized, single-dose, three-way crossover investigation. The study compared the following treatments:
1. Morphine+Ipamorelin;
2. Morphine Control; and
3. Normal Control Plasma samples were obtained over the three hours following acetaminophen administration for determination of acetaminophen AUC as a measure of gastric emptying. It was anticipated that morphine would significantly delay gastric emptying [Yuan 1998]; it was further anticipated that ipamorelin would reverse the observed delay in emptying. The primary parameter of interest is the early absorption of acetaminophen as reflected in the plasma AUC over the first hour following acetaminophen administration ($AUC_{0-60}$). Parameters of additional interest include $AUC_{0-180}$, $C_{MAX}$, and $T_{MAX}$.

The study drug was administered via a well-calibrated infusion pump (e.g., Harvard pump or similar) over a 15 minute period. Each subject's dose was calculated based on body weight to a maximum of 100 kg (6 mg). The dosing volume was then diluted to a total volume of 15 mL using normal saline for injection as the diluent. The syringe was drawn up with an air bubble (to facilitate agitation) and the syringe was mixed by gently inverting six times.

Morphine Administration

Morphine (1.0 mg/mL)/placebo was administered by slow bolus (over 30-60 seconds). The infusion catheter was then flushed immediately with 3-5 mL normal saline.

Acetaminophen Administration

An acetaminophen suspension (32 mg/mL) was shaken well prior to administration. The dose to be administered was 31 mL (992 mg). The subject was then given an additional 150 mL water to drink.

Results

Treatment with ipamorelin was well-tolerated and the results showed a reverse in morphine-induced slowing of gastrointestinal motility in humans. See FIG. 6.

Example 7

Examination of Lower Doses of Ipamorelin in the Morphine-Induced Delay in Gastric Emptying in Healthy Male Volunteers This study was the same design as that of Example 6a but evaluated lower doses of IV ipamorelin to reverse opiate-induced delay in gastric emptying. Data are presented for the twenty three subjects who completed all treatments. The study treatments were: (1) untreated (saline) control; (2) morphine 0.05 mg/kg IV; and (3) morphine 0.05 mg/kg+ipamorelin 0.01 mg/kg IV and (4) morphine 0.05 mg/kg+ipamorelin 0.03 mg/kg IV. Acetaminophen elixir was administered orally in each treatment cycle to permit assessment of gastric emptying. The treatments were administered in a single-blind, placebo-controlled, 3-way crossover study with a washout of 5-8 days between treatments.

Figure 6:
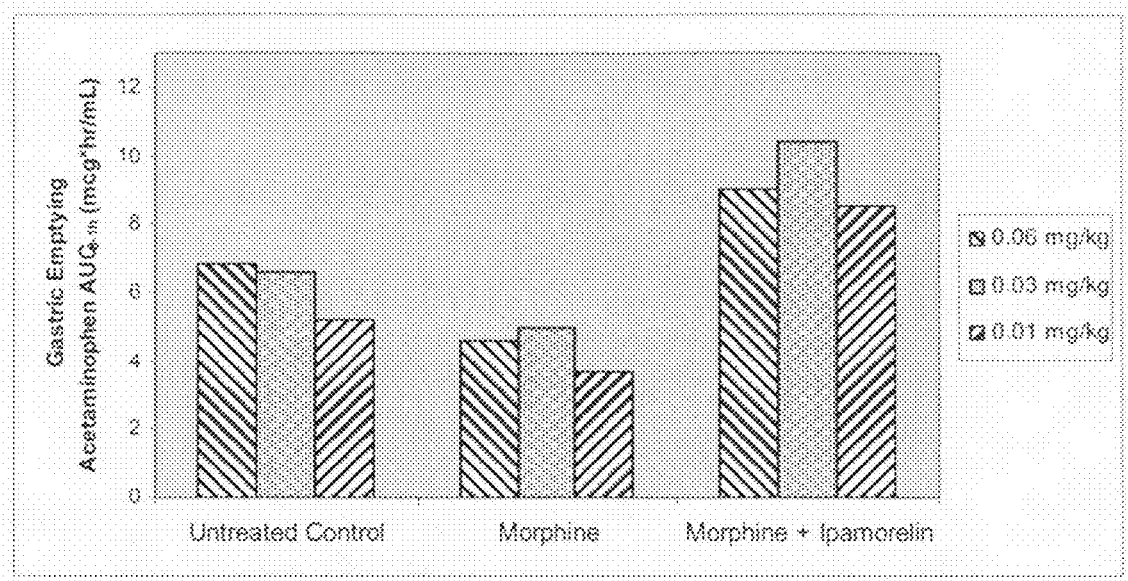
FIG. 6 shows the reversal of morphine-induced slowing of gastrointestinal motility in humans by the intravenous administration of a single dose of ipamorelin at doses of 3 and 0.06 mg/kg.

The results show that administration of morphine delayed gastric emptying as determined by reduced plasma acetaminophen levels. This effect was reversed by both doses of ipamorelin and was comparable to that presented in Example 6. Data are shown in FIG. 6.

Example 8

Comparison of the Effects of Various Ghrelin Mimetics, Including Ipamorelin, on Gastrointestinal Motility in Rats The objective of this study was to evaluate the pharmacological effects of a series of ghrelin mimetics on gastrointestinal motility in rats, as measured by charcoal transit, relative to a commonly used prokinetic agent, metoclopramide, and control, following a single intravenous infusion of the experimental agent.

Treatment groups were as follows:

| Group/<br>Identification | Dose<br>Level<br>(mg/kg) | Dose<br>Concentration<br>(mg/mL) | Dose<br>Volume<br>(mL/kg) | Number of<br>Males |
|---|---|---|---|---|
| 1/Saline control | 0 | 0 | 5 | 8 |
| 2/Metoclopramide | 10 | 1 | 10 | 8 |
| 3/GHRP-6 | 0.25 | 0.05 | 5 | 8 |
| 4/Ghrelin | 0.25 | 0.05 | 5 | 8 |
| 5/Ipamorelin | 0.25 | 0.05 | 5 | 8 |
| 6/RC-1139 acetate | 0.25[a] | 0.05 | 5 | 8 |
| 7/RC-1089 fumarate | 0.25[a] | 0.05 | 5 | 8 |
| 8/RC-1187 acetate | 0.25[a] | 0.05 | 5 | 8 |
| 9/RC-1141 acetate | 0.25[a] | 0.05 | 5 | 8 |

[a]Doses were corrected for the test articles salt/base ratio

Treatment Procedure:

Each dosing formulation was prepared on the day of dosing. For the ghrelin mimetics an aliquot of a 4 mg/mL stock solution was diluted with an appropriate volume of vehicle to achieve the final desired concentration. The reference article formulations were also prepared on the day of dosing by mixing the appropriate amount of reference article with the appropriate volume of vehicle to achieve the desired final concentration. The saline and metoclopramide (1 mg/mL) were used as supplied.

Dosing was performed on consecutive days with approximately equal numbers of animals being dosed on each day. The animals were deprived of food overnight prior to treatment. Each formulation was administered by intravenous injection into the tail vein using a syringe and appropriate gauge needle. The dose volume was 5 mL/kg or 10 mL/kg (in the case of metoclopramide only).

Approximately 30 minutes following dosing with the test article, all animals received 3 mL of activated charcoal by oral gavage, followed by a 20-minute period in which the animals were food and water deprived.

Following the observation period the rats were euthanized, the abdominal cavity opened, and the stomach and intestines removed. The presence or absence of charcoal was documented. The stomachs were weighed (with or without contents) to give an indication of gastric emptying. The intestines were opened and extended to their full length. The charcoal was located and the distances from the pyloric sphincter to the most proximal and distal traces of charcoal were measured as was the total distance from the pyloric sphincter to the cecum. Also, the distance traveled by the charcoal as a percentage of the total length of the small intestine was measured.

Results

Metoclopramide significantly increased intestinal motility, increasing the distal distance traveled by the charcoal meal from 67.3% for the control group to 86.9% for the metoclopramide-treated group, a 29% increase. In contrast, the stomach charcoal content of the group of animals administered metoclopramide was not significantly different from that of the control group.

Ipamorelin significantly increased stomach emptying relative to the control group, reducing the amount of charcoal remaining in the stomach by 66%. Ghrelin and GHRP-6 also significantly reduced the amount of charcoal remaining in the stomach, by 57% and 64%, respectively, relative to the control group, but their effects did not differ significantly from that of ipamorelin.

Figure 7:
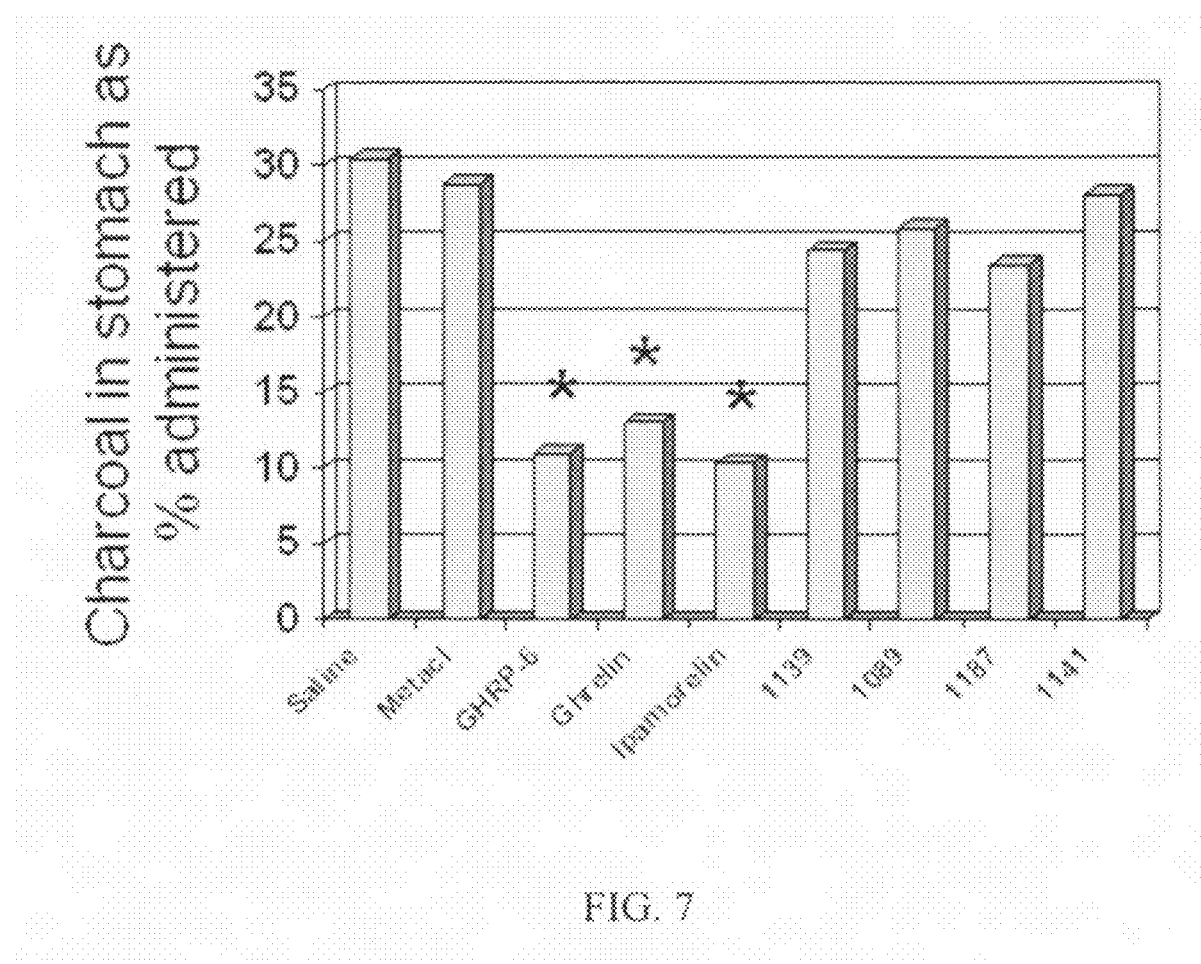
FIG. 7 shows a bar graph comparing the effect of various ghrelin mimetics on stomach emptying.
Figure 8:
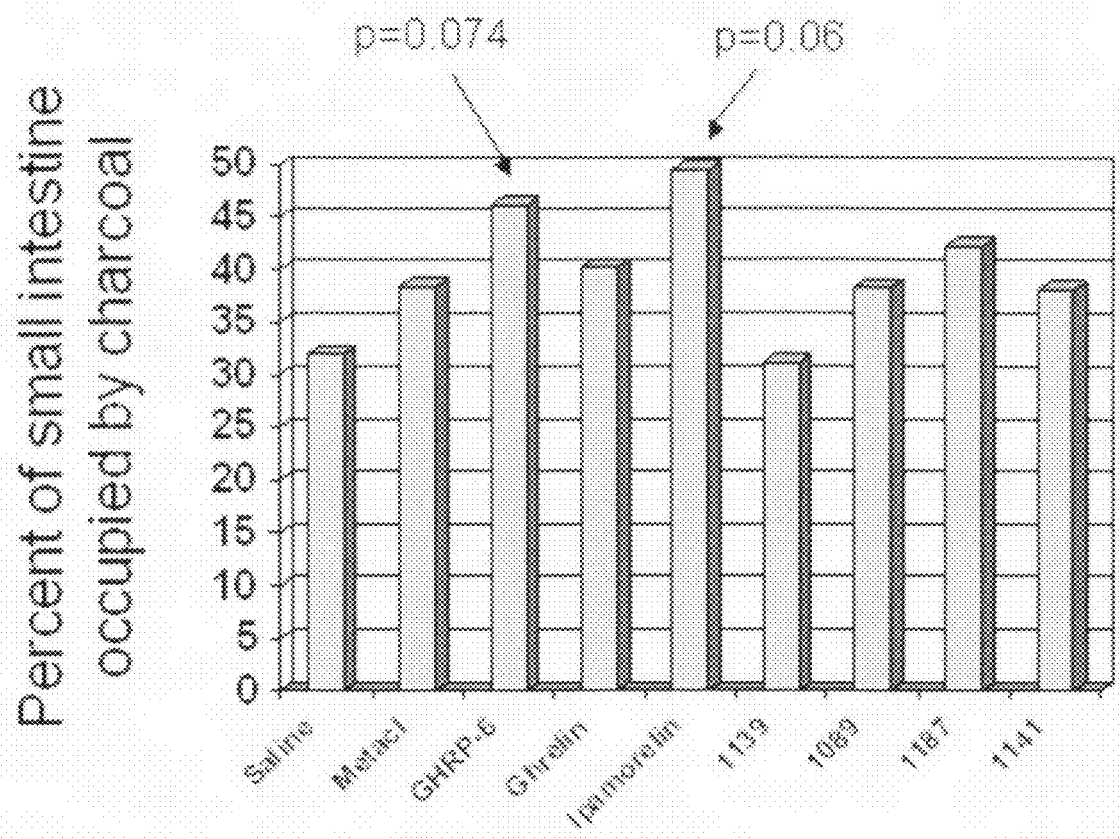
FIG. 8 shows a bar graph comparing the effect of various ghrelin mimetics on gastrointestinal motility through the small intestine.

Ipamorelin clearly produced a highly significant ($P<0.001$) increase in stomach emptying and a tendency towards an increase in intestinal motility compared to saline-treated control group animals, supporting the view that ipamorelin is a potent gastroprokinetic agent. The results of these experiments are set forth in FIGS. 7 and 8.

Example 9

Comparison of the Effects of Various Ghrelin Mimetics, Including Ipamorelin, on Gastrointestinal Motility in Rats The objective of this study was to evaluate the pharmacological effects of a series of ghrelin mimetics on gastrointestinal motility in rats, as measured by charcoal transit, relative to control, following a single intravenous infusion of the experimental agent.

Treatment groups were as follows:

| Group/<br>Identification | Dose Level<br>(μmoles/kg) | Dose Level[a]<br>(mg/kg) | Concentration<br>(μmoles/mL) | Concentration<br>(mg/mL) | Dose Volume<br>(mL/kg) | Number of<br>Males |
|---|---|---|---|---|---|---|
| 1/Saline control | 0 | 0 | 0 | 0 | 5 | 14 |
| 2/Ghrelin | 75 | 0.2486 | 15 | 0.0497 | 5 | 14 |
| 3/GHRP-6 | 75 | 0.0655 | 15 | 0.0131 | 5 | 14 |
| 4/Ipamorelin | 75 | 0.0562 | 15 | 0.0113 | 5 | 14 |
| 5/RC-1139 acetate | 75 | 0.0523 | 15 | 0.0105 | 5 | 14 |

[a]Doses of Ipamorelin and RC-1139 were corrected for their respective purity
[b]Both compounds were co-administered via a single formulation containing the appropriate amount of each compound and dosed as a single injection.

Treatment Procedure:

Dosing commenced on consecutive days with approximately equal numbers of animals from each group being dosed on each day. The animals were food deprived overnight prior to treatment. Prior to dosing, the animals were water deprived. The test/reference/positive control articles were administered by intravenous injection into the tail vein using a syringe and appropriate gauge needle. The dose volume was 5 mL/kg and the actual dose administered was based on the most recent practical body weight of each animal.

Approximately 30 minutes following dosing with the test/ reference or positive control article, all animals received 3 mL of activated charcoal by oral gavage, followed by a 20-minute period during which the animals were food and water deprived.

At the end of the observation period, the rats were euthanized and the abdominal cavity was opened and the stomach and intestines were removed. The presence or absence of charcoal in the stomach was documented. The stomachs were weighed (with and without contents) and this was recorded to give an indication of gastric emptying. The intestines were opened and extended to their full length. The charcoal was located and the distances from the pyloric sphincter to the most proximal and distal traces of charcoal were measured and recorded, as well as the total distance from the pyloric sphincter to the cecum (all distances were measured in mm). In addition to the stomachs weights (with and without contents) the distance traveled by the charcoal as a percentage of the total length of the small intestine was recorded to give an indication of the gastric emptying. Any abnormal or unusual clinical signs noted during the 20-minute observation period were recorded.

Results

Figure 9:
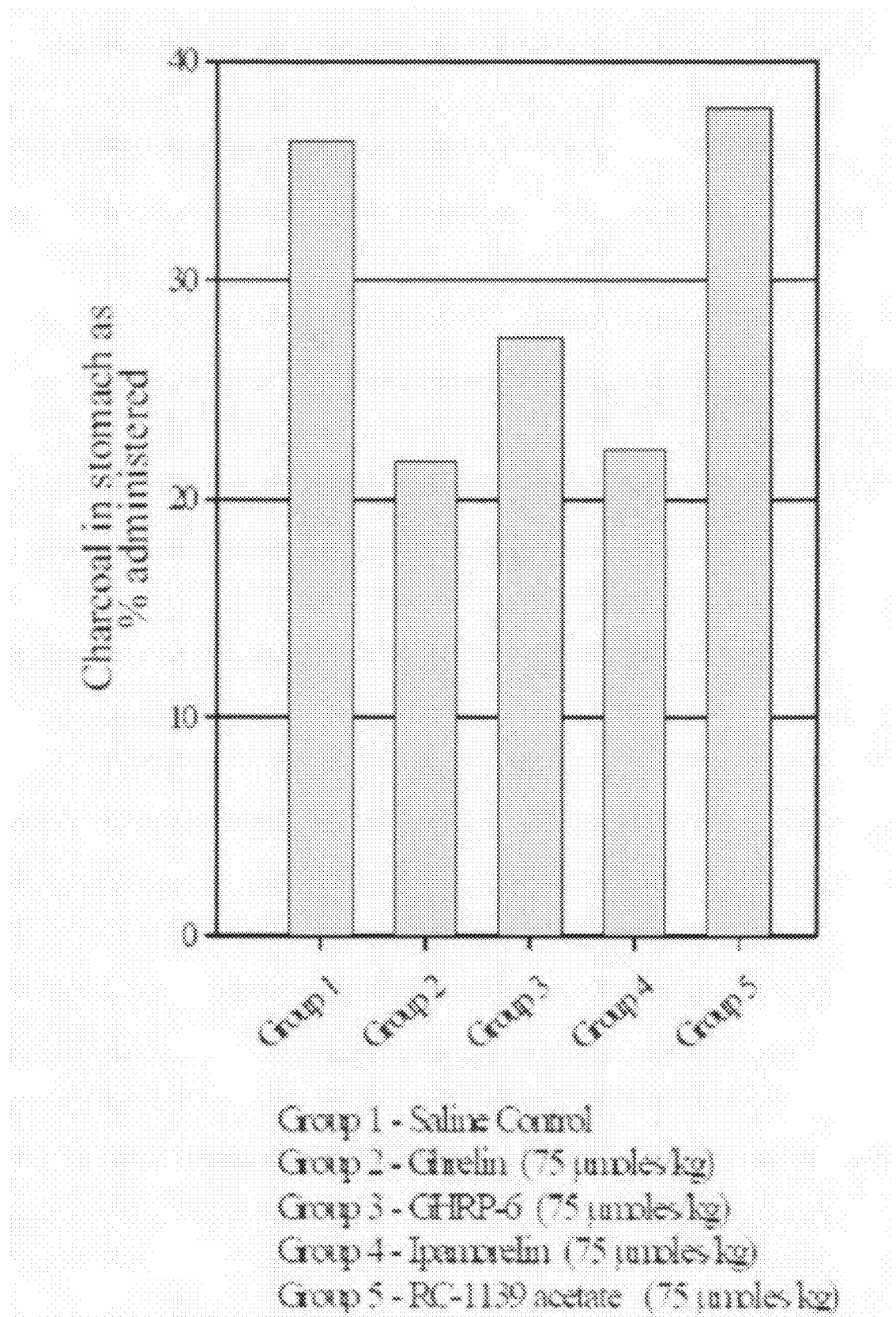
FIG. 9 shows a bar graph comparing the effect of various ghrelin mimetics on stomach emptying.
Figure 10:
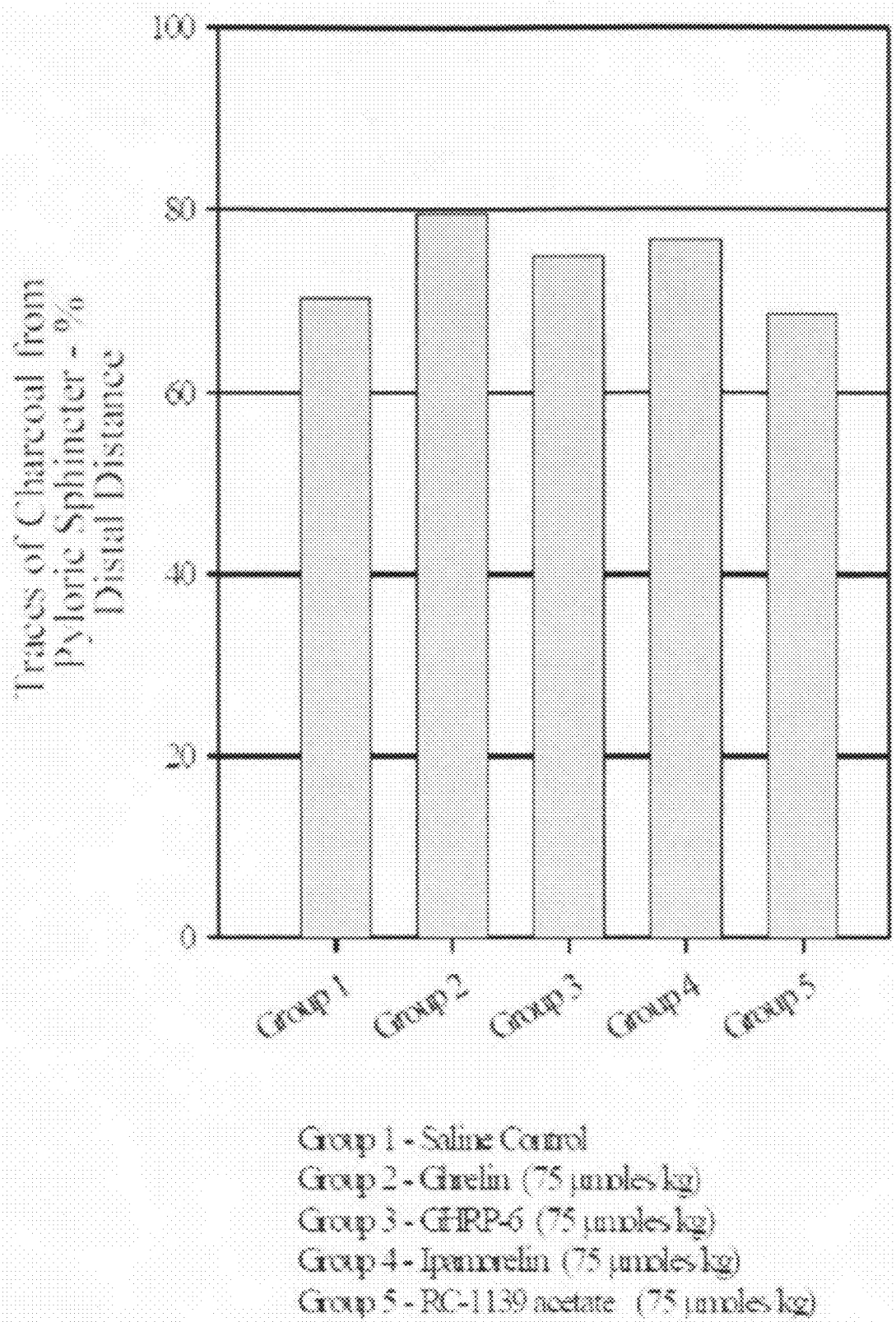
FIG. 10 shows a bar graph comparing the effect of various ghrelin mimetics on gastrointestinal motility through the small intestine (distal distance from pyloric sphincter).
Figure 11:
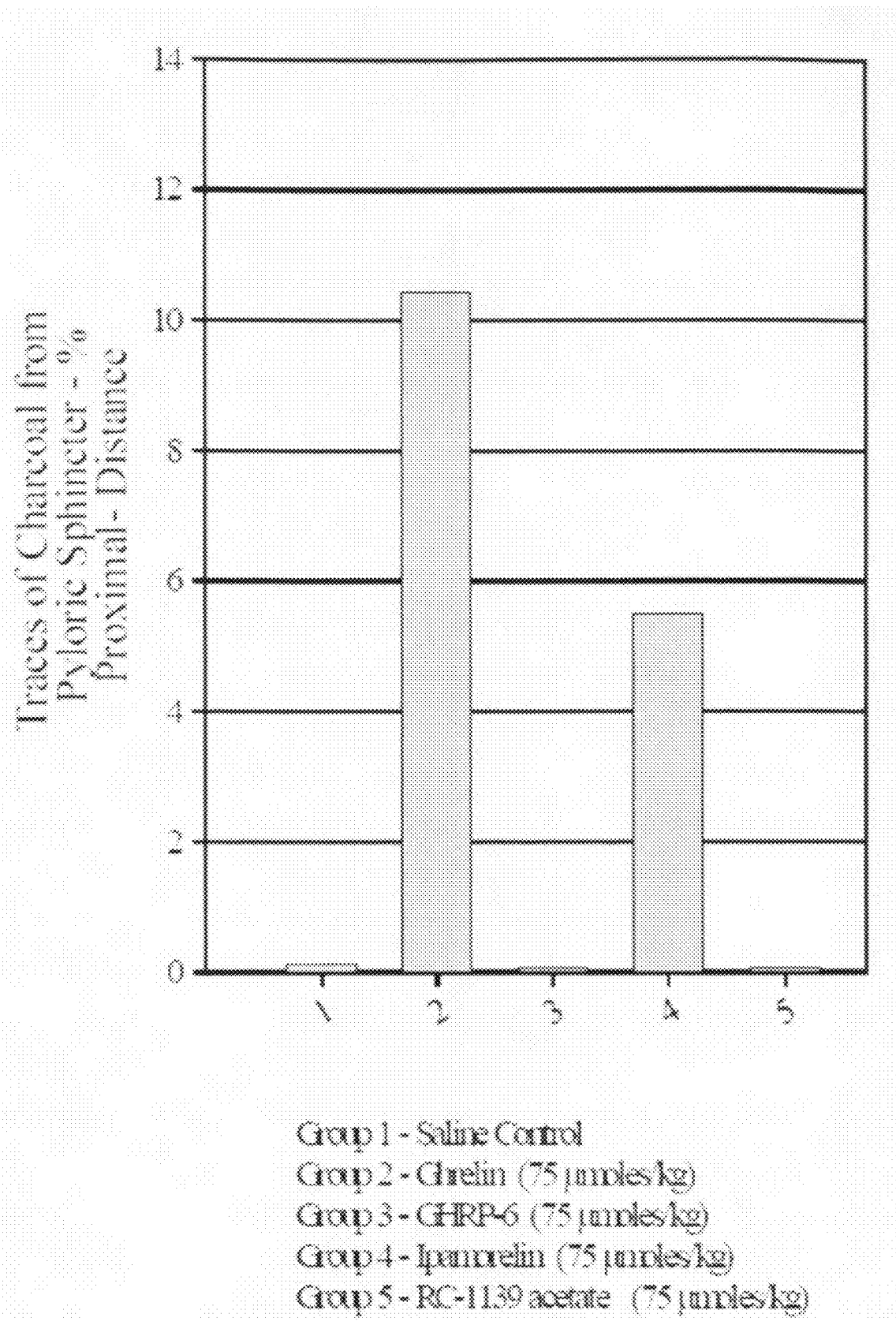
FIG. 11 shows a bar graph comparing the effect of various ghrelin mimetics on gastrointestinal motility through the small intestine (proximal distance from pyloric sphincter).

At a single intravenous dose of 75 μmoles/kg, ghrelin and the three ghrelin mimetics tested in this study (ipamorelin, GHRP-6, and RC-1139 acetate) displayed disparate effects on gastric emptying and intestinal transit in the male albino rat when administered independently. Only ipamorelin displayed similar prokinetic effects to ghrelin on gastric emptying and both measurements of intestinal transit (proximal and distal distances traveled by the charcoal from the pyloric sphincter). Ghrelin, GHRP-6, and ipamorelin resulted in gastric emptying by one of the two measures (proximal distance traveled by the charcoal from the pyloric sphincter) of intestinal transit. See FIGS. 9, 10 and 11.

Example 10

Efficacy of Ipamorelin for the Treatment of Postoperative Ileus in Rats

The objective of this study was to investigate whether ipamorelin would accelerate colonic transit in a rat model of POI. To perform this assessment both single dose and multiple dose efficacy were evaluated.

Materials and Methods

Animals: Adult male Sprague-Dawley rats with indwelling catheters implanted in the right jugular vein were obtained from Charles River (Wilmington, Mass.). The initial body weight of the animals was 250-270 g. The catheters were maintained patent during the acclimation and were used for the dosing of ipamorelin or vehicle. An additional group of control rats, not subjected to surgery and drug or vehicle treatment, were purchased with an indwelling catheter implanted into the proximal colon (1-2 cm from the cecum) used for infusion of a dye marker measuring colonic transit. All rats were single-housed under controlled conditions (25° C., 12 h light/dark cycle) with free access to food and water. An acclimation period of at least one week was allowed prior to the experiments.

Induction of post-operative ileus (POI): POI was induced by a surgical procedure described as "running of the bowel" (Kalff et al., 1998). Specifically, rats were anesthetized with isoflurane (2-3%) inhalation, the abdomen was shaved, disinfected and a midline incision was made to expose the viscera. The small intestine and the cecum were exteriorized and inspected for 5 min using cotton applicators soaked in sterile saline. After completing the inspection, the intestine was covered with gauze soaked in saline and the abdomen remained open for additional 10 min. To study colonic transit, 200 μl of a non-absorbable dye marker (trypan blue in saline) was injected into the proximal colon (1 cm distal to the cecum). The incision was then closed with silk sutures. The whole procedure lasted 25-30 min. Surgeries were always performed at 6:00-8:00 AM and the animals received ipamorelin or vehicle treatment during the light phase of the light/dark cycle.

Measurement of colonic transit time: Prior to the experiments, the rats were fasted for 20-22 h with free access to water. At the end of the surgical procedure the rats received intracolonic injection of the dye marker. Following the surgery the rats were placed in clean home cages supplied with pre-weighed food (Purina rat chow) and water. Colonic transit time was evaluated as the period between the end of surgery and the appearance of dye in the fecal pellet. A naïve rat not subjected to surgery and drug or vehicle treatment was studied on each experimental day together with the rats with POI. The naïve rats were equipped with colonic catheters used to infuse the dye marker into the colon following a 20-22 h fasting. The data collected from these animals served as a reference to healthy controls. In previous studies rats with POI showed a significant delay in colonic transit times compared to naïve animals (Zittel et al., 1998; *Greenwood-Van Meerveld*, unpublished data).

Cumulative fecal output, food intake and body weight: Fecal pellets were counted and weighed at 3-h intervals and 12-h intervals during the first 48 post-surgery (see experimental design). The cumulative fecal output was evaluated by adding the number of pellets throughout a 48-h post-surgical period. Food intake was recorded at 3-h interval or 12-h intervals according to the experimental design and was normalized as g/100 g body weight. The cumulative food intake was calculated for 48 h post-surgery in both series of experiments. Body weight was measured daily at 8:00-9:00 AM before fasting the animals, on the day of experiment before the surgery and at 24 h and 48 h post-surgery. Changes in body weight are expressed as body weight gain compared to the weight of the fasted animal taken before the surgery.

Test and control articles: The test compound ipamorelin (free base) was converted to the diacetate salt by mixing with 2 molar equivalents of glacial acetic acid. Stock solutions of 0.5 mg/ml were prepared daily in sterile saline plus glacial acetic acid (0.1 μp per ml) to bring ipamorelin into solution (pH 3-4). Then the solution was titrated with NaOH to pH 7.0-7.2. Additional dilutions were made in saline. Sterile saline was used in the vehicle control experiments. The positive control [D-Lys$^3$]-GHRP-6 was purchased from Sigma-Aldrich (St. Louis, Mo.) and dissolved in sterile saline. Both the test and control articles were administered as a bolus i.v. infusion via the jugular catheter at a volume of 0.2 ml/100 g body weight.

Data and Statistical Analysis: The data expressed as the mean±SEM for each group. Differences between groups were assessed for statistical significance by Student's T test, as well as by one-way or two-way ANOVA followed by Dunnett's or Bonferroni's test for multiple comparison where appropriate. A level of $p<0.05$ was considered significant. Additionally, the data for the effects of multiple dosing were evaluated using linear regression analysis to determine significant differences between the slopes of the lines between treatments.

EXPERIMENTAL DESIGN:

Experimental Series 1:

Determine the Acute Effects Induced by a Single Dose of Ipamorelin in a Rat Model of POI.
  rats acclimated to the facility for 7 days; patency of catheters maintained
  day 0: rats weighed and fasted at 8:00-9:00 AM
  day 1: at 6:00-8:00 AM "running of the bowel" surgery under isoflurane anesthesia dye infused in to the proximal colon at end of surgery single-dose treatment with ipamorelin or vehicle observation in home cage (time to first fecal pellet; fecal output and food intake at 3, 6, 9, and 12 h post-surgery)

day 2: 7:00-8:00 AM body weight, fecal output, food intake at 24-h post-surgery day 3: 7:00-8:00 AM body weight, fecal output, food intake at 48-h post-surgery euthanized with overdose of isoflurane Naïve rats were fasted but not subjected to surgery. Body weight, colonic transit, fecal pellet output and food intake were measured at the same time points as in rats with POI.

Groups (single dose treatment):

| | |
|---|---|
| POI + vehicle i.v.) | n = 12 |
| POI + ipamorelin 0.1 mg/kg (i.v.) | n = 9 |
| POI + ipamorelin 1 mg/kg (i.v.) | n = 10 |
| POI + GHRP-6 20 µg/kg (i.v.) | n = 8 |
| Naïve (no surgery, no drug) | n = 14 |

Experimental Series 2:

Determine the Efficacy of Multiple Doses of Ipamorelin in a Rat Model of POI.

rats acclimated to the facility for 7 days; patency of catheters maintained day 0: rats weighed and fasted at 8:00-9:00 AM day 1: at 6:00-8:00 AM "running of the bowel" surgery under isoflurane anesthesia dye infused in to the proximal colon at end of surgery multiple dosing of ipamorelin or vehicle ($1^{st}$ dose at end of surgery, $2^{nd}$, $3^{rd}$ and $4^{th}$ dose at 3-h intervals)

observation in home cage (time to first fecal pellet, fecal output, food intake at 3, 6, 9 and 12 h post-surgery)

day 2: 7:00-8:00 AM body weight at 24-h post surgery multiple dosing of ipamorelin or vehicle ($1^{st}$ dose after measuring body weight, $2^{nd}$, $3^{rd}$ and $4^{th}$ dose at 3-h intervals)

observation in home cage (fecal output, food intake at 24, 27, 30, 33 and 36 h post-surgery)

day 3: 7:00-8:00 AM body weight, fecal output, food intake at 48-h post surgery euthanasia with isoflurane overdose Naïve rats were fasted but not subjected to surgery. Body weight, colonic transit, fecal pellet output and food intake were measured at the same time points as in rats with POI. Note that the naïve animals remained in their home cage and were not handled in contrast to the rats with POI, which were handled multiple times during the dosing of ipamorelin or vehicle.

Groups (Multiple Dosing):

| | |
|---|---|
| POI + vehicle (i.v.) | n = 8 |
| POI + ipamorelin 0.01 mg/kg (i.v.) | n = 8 |
| POI + ipamorelin 0.1 mg/kg (i.v.) | n = 8 |
| POI + ipamorelin 1 mg/kg (i.v.) | n = 7 |
| Naïve (no surgery, no drug) | n = 8 |

Results

POI in the rat: Effect of abdominal surgery on colonic transit time, fecal pellet output, food intake and body weight.

Figure 12:
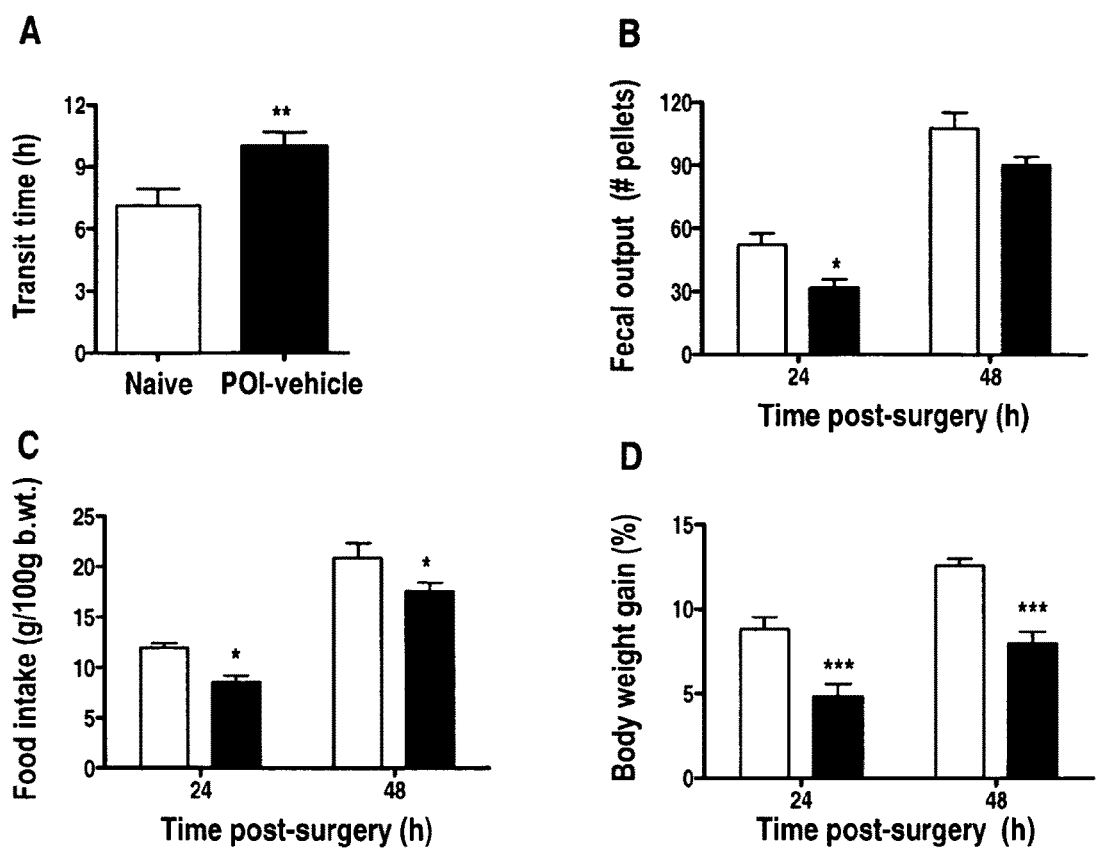
FIG. 12A-D show the effect of abdominal surgery on colonic transit time, fecal pellet output, food intake, and body weight gain in rat model of post-operative ileus.

A comparison between rats subjected to "running of the bowel" surgery and naïve rats demonstrated that surgery results in the development of POI characterized as a delay in colonic transit (FIG. 12A), a decrease in fecal pellet output (FIG. 12 B), decreased food intake (FIG. 12 C) and body weight gain (FIG. 12 D).

The rat model of POI. (A) Colonic transit time, measured as the time to the first marked fecal pellet, is significantly delayed following surgery compared to naïve rats. (B) The cumulative fecal pellet output at 24 h and 48 h post-surgery is reduced compared to naïve rats (C) Cumulative food intake is significantly decreased at 24 h and 48 h post surgery compared to naïve rats. (D) Body weight gain is reduced following surgery compared to naïve rats. Data are mean±SEM from 12 rats with POI and 14 naïve rats. Significance of the differences between rats subjected to surgery and naïve rats was tested using Student t-test: * $p<0.05$,  $p<0.01$, * $p<0.001$.

Experimental Series 1:

Determine the Acute Effects Induced by a Single Dose Treatment with Ipamorelin in a Rat Model of POI.

Figure 13:
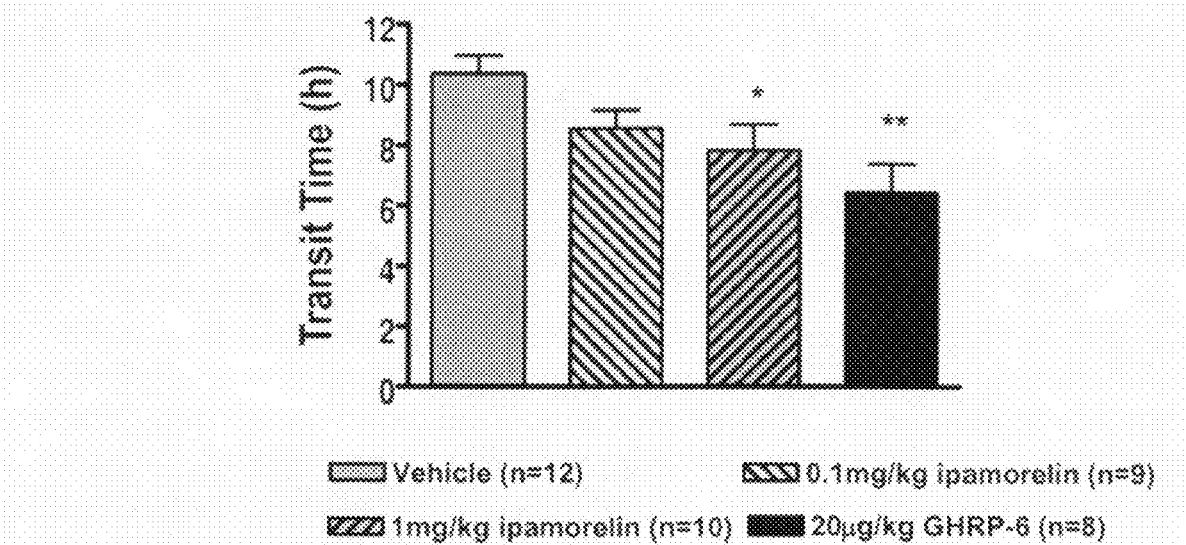
FIG. 13 shows colonic transit time in rats after abdominal surgery after single dose administration of ipamorelin at 0.1 and 1 mg/kg relative to vehicle and a control (GHRP-6).
Figure 14:
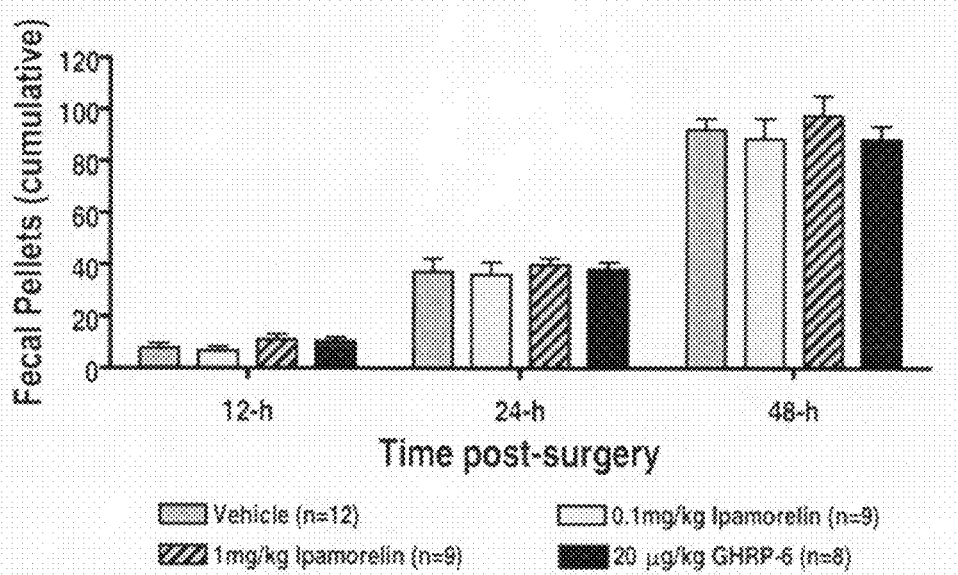
FIG. 14 shows cumulative fecal pellet output at 12 h, 24 h or 48 h in rats after abdominal surgery after single dose administration of ipamorelin at 0.1 and 1 mg/kg relative to vehicle and a standard control (GHRP-6).
Figure 15:
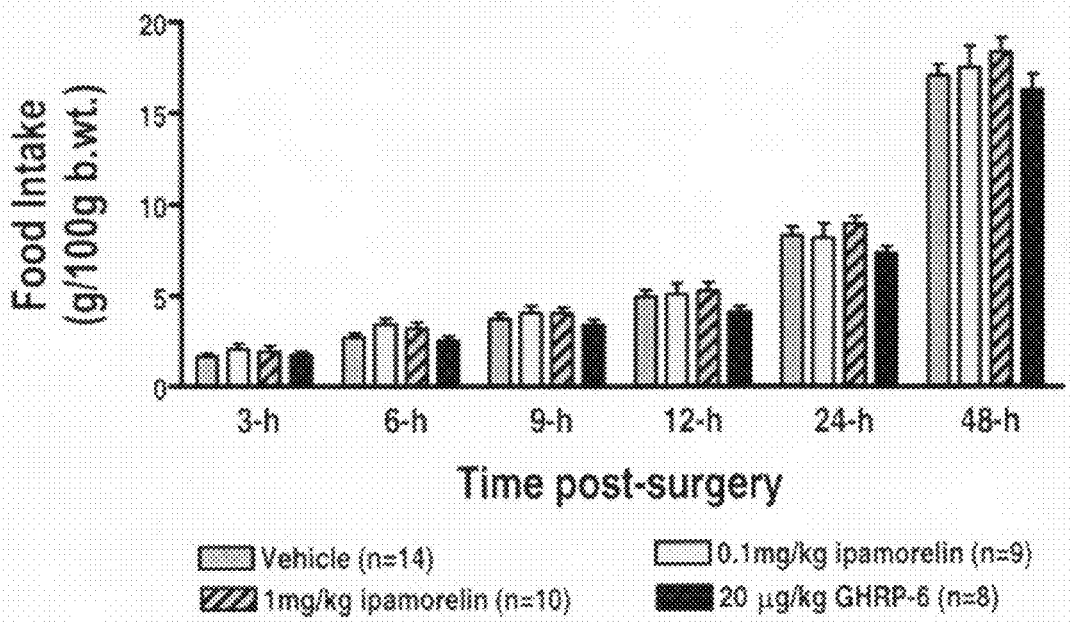
FIG. 15 shows cumulative food intake at different time points between 3-48 h in rats after abdominal surgery after single dose administration of ipamorelin at 0.1 and 1 mg/kg relative to vehicle and a standard control (GHRP-6).
Figure 16:
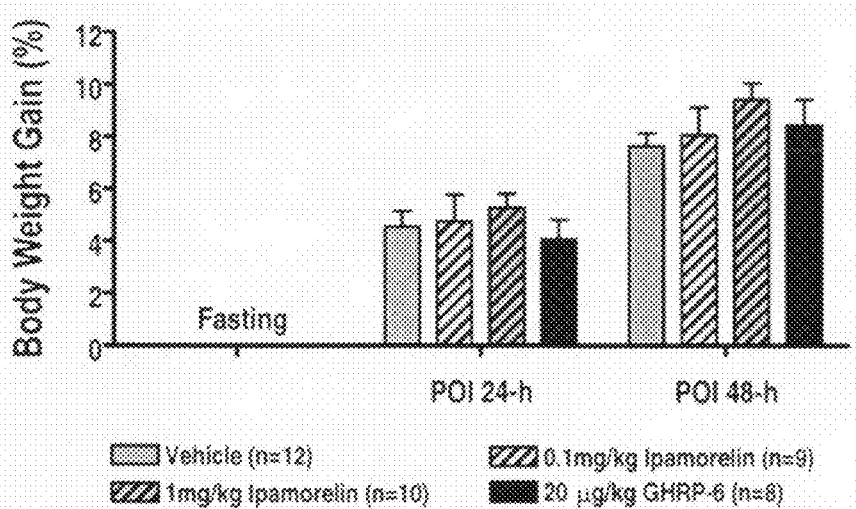
FIG. 16 shows the effect on body weight at 24 h and 48 h in rats after abdominal surgery after single dose administration of ipamorelin at 0.1 and 1 mg/kg relative to vehicle and a standard control (GHRP-6).

Experiments were performed in rats with POI to investigate the efficacy of a single-dose treatment with 0.1 mg/kg or 1 mg/kg ipamorelin. Ipamorelin or the vehicle was administered via i.v. infusion following the end of the surgery. The time to the first fecal pellet (FIG. 13), as well as cumulative fecal pellet output (FIG. 14), food intake (FIG. 15) and body weight gain (FIG. 16) were measured during the first 48 h post-surgery and the efficacy of ipamorelin was evaluated by comparing the effects of ipamorelin to the effect of the vehicle. In addition, the effect of 20 µg GHPR-6, an agonist of GRLN, i.e., GHS-$R_{1a}$ was used as a positive control (Davenport et al., 2005). The results presented in FIG. 13 demonstrate that a single post-surgical dose of 1 mg/kg ipamorelin or 20 µg GHRP-6 significantly decreased the colonic transit time.

However, neither ipamorelin nor GHRP-6 had a significant effect on fecal pellet output (FIG. 14) food intake (FIG. 15) or body weight gain (FIG. 16) during the first 48 h post-surgery.

In summary, the results obtained in Experimental series 1 demonstrate that a single-dose treatment with 1 mg/kg ipamorelin given at the end of surgery decreased the time to the first bowel movement, but did not induce effects on fecal output and food intake during the 48-h course of recovery in rats with POI. However, these results are consistent with those expected based on the reported half-life of ipamorelin in the rat of 30-60 minutes. (Johansen et. al., 1998).

Experimental Series 2:

Determine the Efficacy of Multiple Doses of Ipamorelin in a Rat Model of POI.

Figure 17:
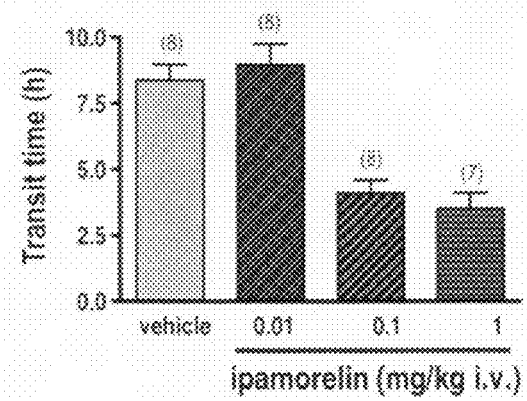
FIG. 17 shows colonic transit time in rats after abdominal surgery after multiple doses of 0.01, 0.1 and 1.0 mg/kg ipamorelin relative to vehicle.

The dose-response effect of multiple doses of ipamorelin (0.01, 0.1 or 1 mg/kg i.v.) was investigated in rats with POI. The results showed that the multiple dosing of 0.1 mg/kg or 1 mg/kg ipamorelin caused a significant acceleration of colonic transit compared to the effect of the vehicle (FIG. 17).

Figure 18:
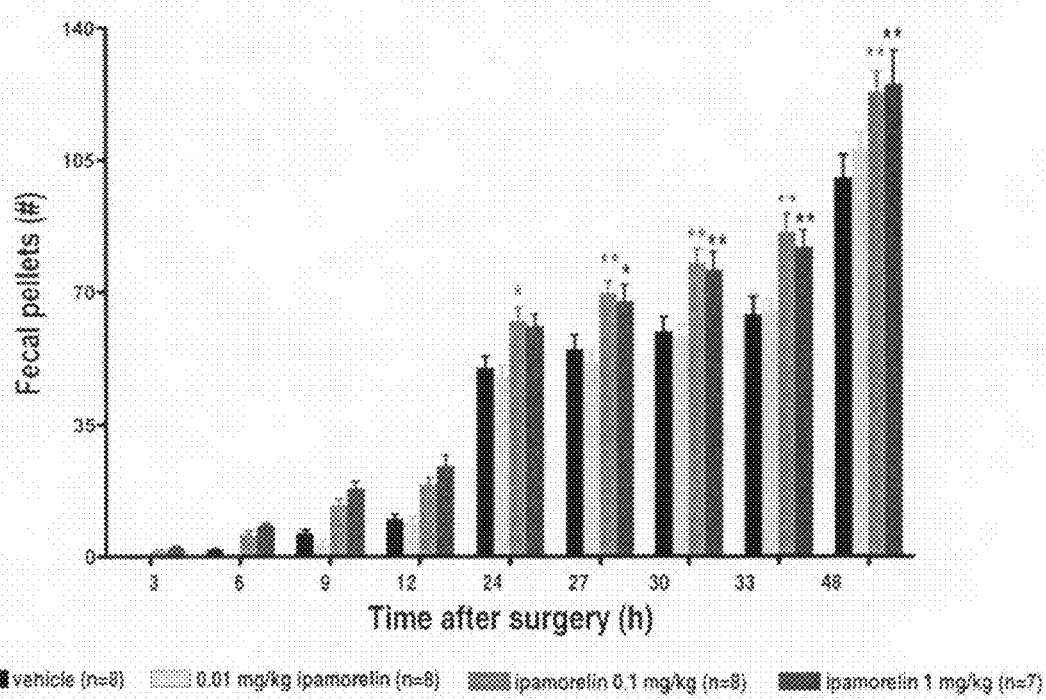
FIG. 18 shows the effect of fecal pellet output over a 48 h period in rats after abdominal surgery after multiple doses of ipamorelin at 0.01 and 1.0 mg/kg ipamorelin relative to vehicle.
Figure 19:
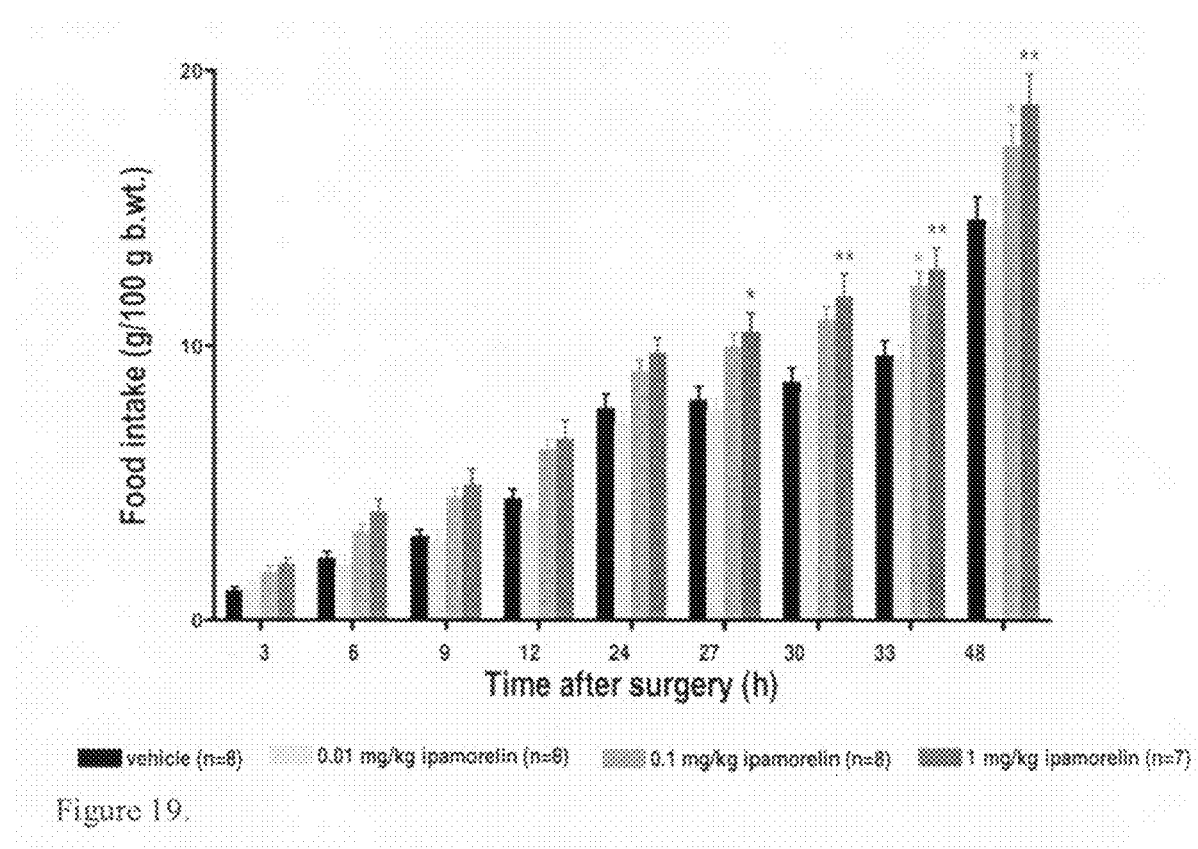
FIG. 19 shows the effect on cumulative food intake over a 48 h period in rats after abdominal surgery after multiple doses of ipamorelin at 0.01 and 1.0 mg/kg ipamorelin relative to vehicle.
Figure 20:
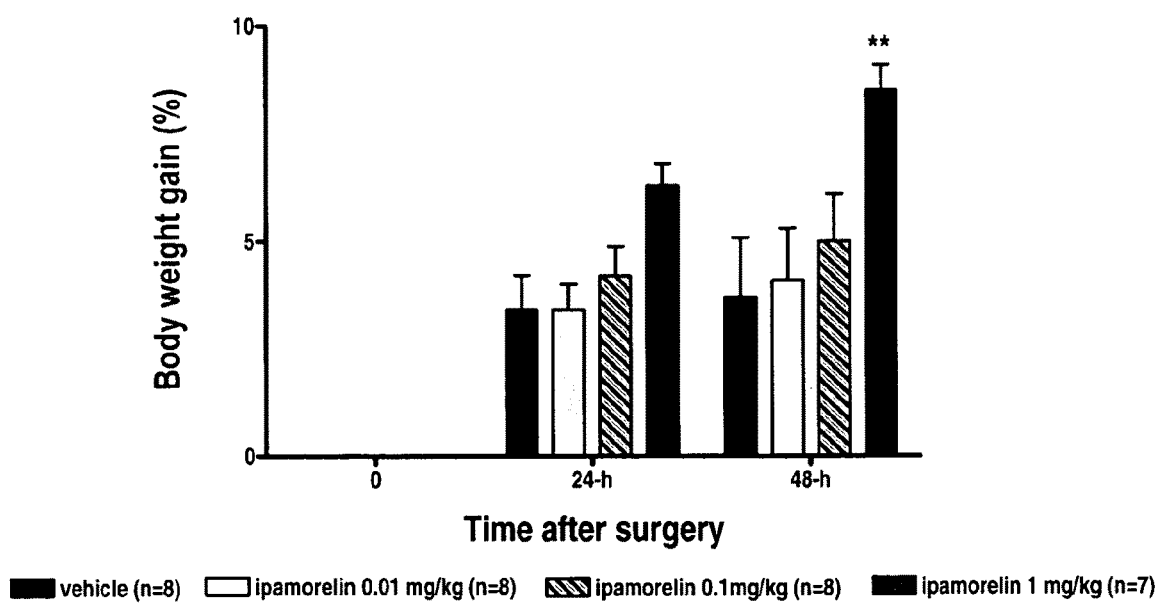
FIG. 20 shows the effect on body weight gain over a 48 h period in rats after abdominal surgery after multiple doses of ipamorelin at 0.01, 0.1 and 1.0 mg/kg ipamorelin relative to vehicle.

The effects of multiple doses of ipamorelin on fecal pellet output are presented in FIG. 18. Multiple doses of ipamorelin induced an increase in cumulative fecal pellet output compared to the vehicle. The effect reached significance at doses of 0.1 mg/kg or 1 mg/kg (FIG. 18). Fecal output increased at a higher rate (lower 1/slope values) in the rats receiving ipamorelin at doses of 0.1 or 1 mg/kg i.v. compared to rats treated with vehicle. At a dose of 0.01 mg/kg, ipamorelin showed no significant effect. In addition, ipamorelin induced an increase food intake (FIG. 19). The increase in food intake induced by the higher doses of ipamorelin was associated with an increase in body weight. As illustrated in FIG. 20, the rats receiving the highest dose of 1 mg/kg ipamorelin, administered according to the multiple dosing paradigm, gained significantly more body weight during the first 48 h after surgery compared to the rats treated with the vehicle.

conclusion

Overall, the results demonstrate that multiple i.v. dosing of ipamorelin in rats during the first 48-h after surgery improves colonic transit and food intake and increases body weight gain suggesting that post-surgical i.v. infusions of ipamorelin may ameliorate the symptoms in patients with POI.

* * *

Having now fully provided the instant disclosure, it will be appreciated by those skilled in the art that the same can be performed within a wide range of equivalent parameters, concentrations, and conditions without departing from the spirit and scope of the disclosure and without undue experimentation. Further, while the disclosure has been described in connection with specific embodiments thereof, it will be understood that it is capable of further modifications. This application is intended to cover any variations, uses, or adaptations of the disclosure following, in general, the disclosed principles and including such departures from the disclosure as come within known or customary practice within the art to which the disclosure pertains and as may be applied to the essential features hereinbefore set forth.

REFERENCES

Asakawa A, Inui A, Kaga T, Yuzuriha H, Nagata T, Ueno N, et al. Ghrelin is an appetitestimulatory signal from stomach with structural resemblance to motilin. Gastroenterology, 2001 February; 120(2):337-45.

Masuda Y, Tanaka T, Inomata N, Ohnuma N, Tanaka S, Itoh Z, et al. Ghrelin stimulates gastric acid secretion and motility in rats. Biochem Biophys Res Commun 2000 Oct. 5; 276(3): 905-8.

Murphy D B, Sutton J A, Prescott L, Murphy M B, Opioid-induced Delay in Gastric Emptying: A Peripheral Mechanism in Humans. Anesthesiology 1997 October; (4)765-70.

Peeters T L. Central and peripheral mechanisms by which ghrelin regulates gut motility. J Physiol Pharmacol 2003 December; 54 Suppl 4:95-103.

Poitras P, Polvino W J, Rocheleau B. Gastrokinetic effect of ghrelin analog RC-1139 in the rat. Effect on post-operative and on morphine induced ileus. Peptides. 2005 September; 26(9): 1598-601.

Tack J, Depoortere I, Bisschops R, Delporte C, Coulie B, Meulemans A, et al. Influence of ghrelin on interdigestive gastrointestinal motility in humans. Gut 2006 March; 55(3): 327-33.

Trudel L, Tomasetto C, Rio M C, Bouin M, Plourde V, Eberling P, et al. Ghrelin/motilinrelated peptide is a potent prokinetic to reverse gastric postoperative ileus in rat. AmJ Physiol Gastrointest Liver Physiol 2002 June; 282(6): G948-G952.

Yuan C S, Foss J F, O'Connor M, Roizen M F, Moss J. Effects of low-dose morphine on gastric emptying in healthy volunteers. J Clin Pharmacol. 1998 November; 38(11):1017-20.

What is claimed is:

1. A method of treating opioid-induced gastroparesis in a human subject in need thereof comprising administering to said subject a therapeutically effective amount of a compound represented by the structural Formula I:

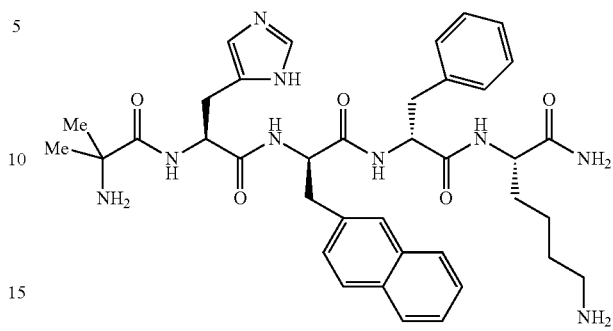

or a pharmaceutically acceptable salt thereof.

2. The method of claim 1, wherein the subject is using an opioid for post-surgical pain management.

3. The method of claim 1, wherein the subject is using an opioid for chronic pain management.

4. The method of claim 3, wherein the opioid is selected from the group consisting of morphine, codeine, oxycodone, hydromorphone, hydrocodone, methadone, and fentanyl.

5. The method of claim 1, wherein the compound is administered in a manner in order to achieve an effective plasma concentration.

6. A method of stimulating the motility of the gastrointestinal system in a human subject suffering from opioid-induced gastroparesis comprising administering to said subject a therapeutically effective amount of a compound represented by the structural Formula I:

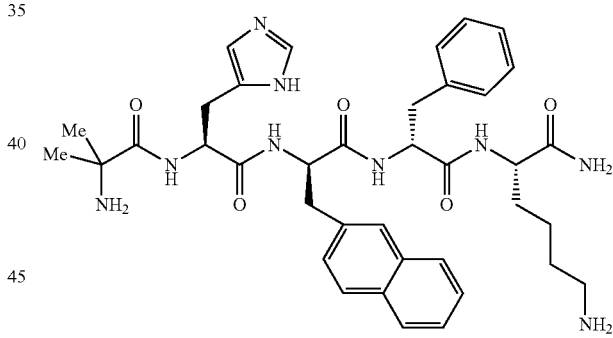

or a pharmaceutically acceptable salt thereof.

7. The method of claim 6, wherein the compound is administered in a manner to achieve an effective plasma concentration.

8. The method of claim 1, consisting essentially of administering said compound or a pharmaceutically acceptable salt thereof.

9. The method of claim 6, consisting essentially of administering said compound or a pharmaceutically acceptable salt thereof.

10. The method of claim 1, wherein said administration is via injection.

11. The method of claim 6, wherein said administration is via injection.

* * * * *